(12) United States Patent
Bruce et al.

(10) Patent No.: US 11,666,339 B2
(45) Date of Patent: Jun. 6, 2023

(54) CIRCULAR SURGICAL STAPLER FOR FORMING CROSS-PATTERN OF STAPLES

(71) Applicant: Cilag GmbH International, Zug (CH)

(72) Inventors: John Kevin Bruce, Morrow, OH (US); John Scott Kimsey, Walton, KY (US); Yvan D. Nguetio Tchoumkeu, Blue Ash, OH (US); Morgan R. Hunter, Cincinnati, OH (US); Cory Kimball, Hamilton, OH (US); Gregory J. Bakos, Mason, OH (US); Christopher Q. Seow, Cincinnati, OH (US); Pierre Mesnil, Newport, KY (US); Laura S. Downing, Cincinnati, OH (US); Jeffery Bruns, Cincinnati, OH (US); Ryan W. McGhee, Cincinnati, OH (US); Chester O. Baxter, III, Loveland, OH (US); John E. Feds, Milford, OH (US); Michael J. Stokes, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/401,460

(22) Filed: Aug. 13, 2021

(65) Prior Publication Data
US 2023/0048389 A1 Feb. 16, 2023

(51) Int. Cl.
*A61B 17/064* (2006.01)
*A61B 17/115* (2006.01)
(Continued)

(52) U.S. Cl.
CPC ....... *A61B 17/1155* (2013.01); *A61B 17/1114* (2013.01); *A61B 2017/00477* (2013.01); *A61B 2017/1157* (2013.01)

(58) Field of Classification Search
CPC .................. A61B 17/1155; A61B 2017/07257
See application file for complete search history.

(56) References Cited

U.S. PATENT DOCUMENTS

| 4,047,654 A | 9/1977 | Alvarado |
| 4,848,328 A | 7/1989 | Laboureau et al. |

(Continued)

FOREIGN PATENT DOCUMENTS

| EP | 1875870 A1 | 1/2008 |
| EP | 2157918 | 3/2010 |

(Continued)

OTHER PUBLICATIONS

U.S. Appl. No. 17/401,391, entitled, "Methods of Forming an Anastomosis Between Organs with an Expandable Pattern," filed Aug. 13, 2021.

(Continued)

*Primary Examiner* — Eyamindae C Jallow
(74) *Attorney, Agent, or Firm* — Frost Brown Todd LLP

(57) ABSTRACT

A surgical stapling instrument includes an anvil defining a plurality of staple forming pockets and a stapling head assembly configured to drive a plurality of staples against the staple forming pockets of the anvil. The stapling head assembly comprises a coupling member configured to actuate the anvil relative to the stapling head assembly, a firing assembly configured to drive the plurality of staples against the staple forming pockets of the anvil, and a deck member. The deck member includes a deck surface extending radially between an inner circular edge and an outer circular edge, and a plurality of staple openings extending through the deck surface. The plurality of staple openings define at least one cross shape.

20 Claims, 24 Drawing Sheets

(51) Int. Cl.
*A61B 17/11* (2006.01)
*A61B 17/00* (2006.01)

(56) References Cited

U.S. PATENT DOCUMENTS

| | | | |
|---|---|---|---|
| 5,292,053 | A | 3/1994 | Bilotti et al. |
| 5,333,773 | A | 8/1994 | Main et al. |
| 5,350,104 | A | 9/1994 | Main et al. |
| 5,533,661 | A | 7/1996 | Main et al. |
| 6,616,686 | B2 | 9/2003 | Coleman et al. |
| 7,056,330 | B2 | 6/2006 | Gayton |
| 7,422,138 | B2 | 9/2008 | Bilotti et al. |
| 7,824,426 | B2 | 11/2010 | Racenet et al. |
| 8,143,870 | B2 | 3/2012 | Ng et al. |
| 8,328,063 | B2 | 12/2012 | Milliman et al. |
| 8,613,384 | B2 | 12/2013 | Pastorelli et al. |
| 8,789,738 | B2 | 7/2014 | Knodel et al. |
| 8,910,847 | B2 | 12/2014 | Nalagatla et al. |
| 9,016,541 | B2 | 4/2015 | Viola et al. |
| 9,192,387 | B1 | 11/2015 | Holsten et al. |
| 9,402,628 | B2 | 8/2016 | Beardsley |
| 9,713,469 | B2 | 7/2017 | Leimbach et al. |
| 9,782,171 | B2 | 10/2017 | Viola |
| 9,848,874 | B2 | 12/2017 | Kostrzewski |
| 9,907,552 | B2 | 3/2018 | Measamer et al. |
| 9,936,949 | B2 | 4/2018 | Measamer et al. |
| 10,285,705 | B2 | 5/2019 | Shelton, IV et al. |
| 10,639,040 | B2 | 5/2020 | Penna et al. |
| 10,709,452 | B2 | 7/2020 | DiNardo et al. |
| 10,925,607 | B2 | 2/2021 | Penna et al. |
| 11,241,232 | B2 | 2/2022 | Guerrera |
| 11,284,890 | B2 | 3/2022 | Nalagatla et al. |
| 2006/0291981 | A1 | 12/2006 | Viola et al. |
| 2011/0011916 | A1 | 1/2011 | Levine |
| 2014/0027493 | A1 | 1/2014 | Jankowski |
| 2014/0158747 | A1* | 6/2014 | Measamer ......... A61B 17/0644 227/179.1 |
| 2015/0083772 | A1 | 3/2015 | Miller et al. |
| 2016/0278768 | A1 | 9/2016 | Johnson et al. |
| 2017/0119397 | A1 | 5/2017 | Harris et al. |
| 2017/0281187 | A1* | 10/2017 | Shelton, IV ....... A61B 17/1155 |
| 2018/0132849 | A1 | 5/2018 | Miller et al. |
| 2018/0235635 | A1 | 8/2018 | Rekstad et al. |
| 2018/0242974 | A1 | 8/2018 | Guerrera et al. |
| 2018/0325508 | A1 | 11/2018 | Aronhalt et al. |
| 2019/0328390 | A1* | 10/2019 | Harris ............... A61B 17/07292 |
| 2020/0038017 | A1 | 2/2020 | Hess et al. |
| 2020/0054339 | A1 | 2/2020 | Scirica et al. |
| 2020/0205835 | A1* | 7/2020 | Nalagatla ................ B21K 5/00 |
| 2020/0229814 | A1 | 7/2020 | Amariglio et al. |
| 2020/0281595 | A1* | 9/2020 | Wise .................. A61B 17/1114 |

FOREIGN PATENT DOCUMENTS

| | | | |
|---|---|---|---|
| EP | | 2649949 A1 | 10/2013 |
| EP | | 3225176 A1 | 10/2017 |
| EP | | 3225179 A1 | 10/2017 |
| EP | | 3245958 A1 | 11/2017 |
| EP | | 3130292 B1 | 8/2018 |
| EP | | 3173030 B1 | 10/2019 |
| EP | | 3643252 A1 | 4/2020 |
| WO | WO 2001/054594 A1 | | 8/2001 |
| WO | WO 2002/009595 A1 | | 2/2002 |
| WO | WO 2005/115254 A2 | | 12/2005 |
| WO | WO 2008/141288 A1 | | 11/2008 |
| WO | WO 2020/249487 A1 | | 12/2020 |

OTHER PUBLICATIONS

U.S. Appl. No. 17/401,428, entitled, "Staple Forming Features for Circular Surgical Stapler," filed Aug. 13, 2021.
U.S. Appl. No. 17/401,430, entitled, "Non-Circular End Effector Features for Surgical Stapler," filed Aug. 13, 2021.
U.S. Appl. No. 17/401,439, entitled, "Circular Surgical Stapler End Effector Having Staple Line Alignment Feature," filed Aug. 13, 2021.
U.S. Appl. No. 17/401,444, entitled, "Circular Surgical Stapler for Forming Pattern of Non-Tangential Staples," filed Aug. 13, 2021.
U.S. Appl. No. 17/401,451, entitled, "Circular Surgical Stapler Having Staples with Expandable Crowns," filed Aug. 13, 2021.
U.S. Appl. No. 17/401,391.
U.S. Appl. No. 17/401,428.
U.S. Appl. No. 17/401,430.
U.S. Appl. No. 17/401,439.
U.S. Appl. No. 17/401,444.
U.S. Appl. No. 17/401,451.
U.S. Appl. No. 17/489,965.
International Search Report and Written Opinion dated Nov. 14, 2022 for Application No. PCT/IB2022/057444, 12 pgs.
International Search Report and Written Opinion dated Jan. 27, 2023 for Application No. PCT/IB2022/057446, 19 pgs.
International Search Report and Written Opinion dated Nov. 23, 2022 for Application No. PCT/IB2022/057449, 15 pgs.
International Search Report and Written Opinion dated Jan. 25, 2023 for Application No. PCT/IB2022/057442, 20 pgs.
International Search Report and Written Opinion dated Nov. 14, 2022 for Application No. PCT/IB2022/057443, 12 pgs.
International Search Report and Written Opinion dated Nov. 24, 2022 for Application No. PCT/IB2022/057451, 13 pgs.

* cited by examiner

CIRCULAR SURGICAL STAPLER FOR FORMING CROSS-PATTERN OF STAPLES

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
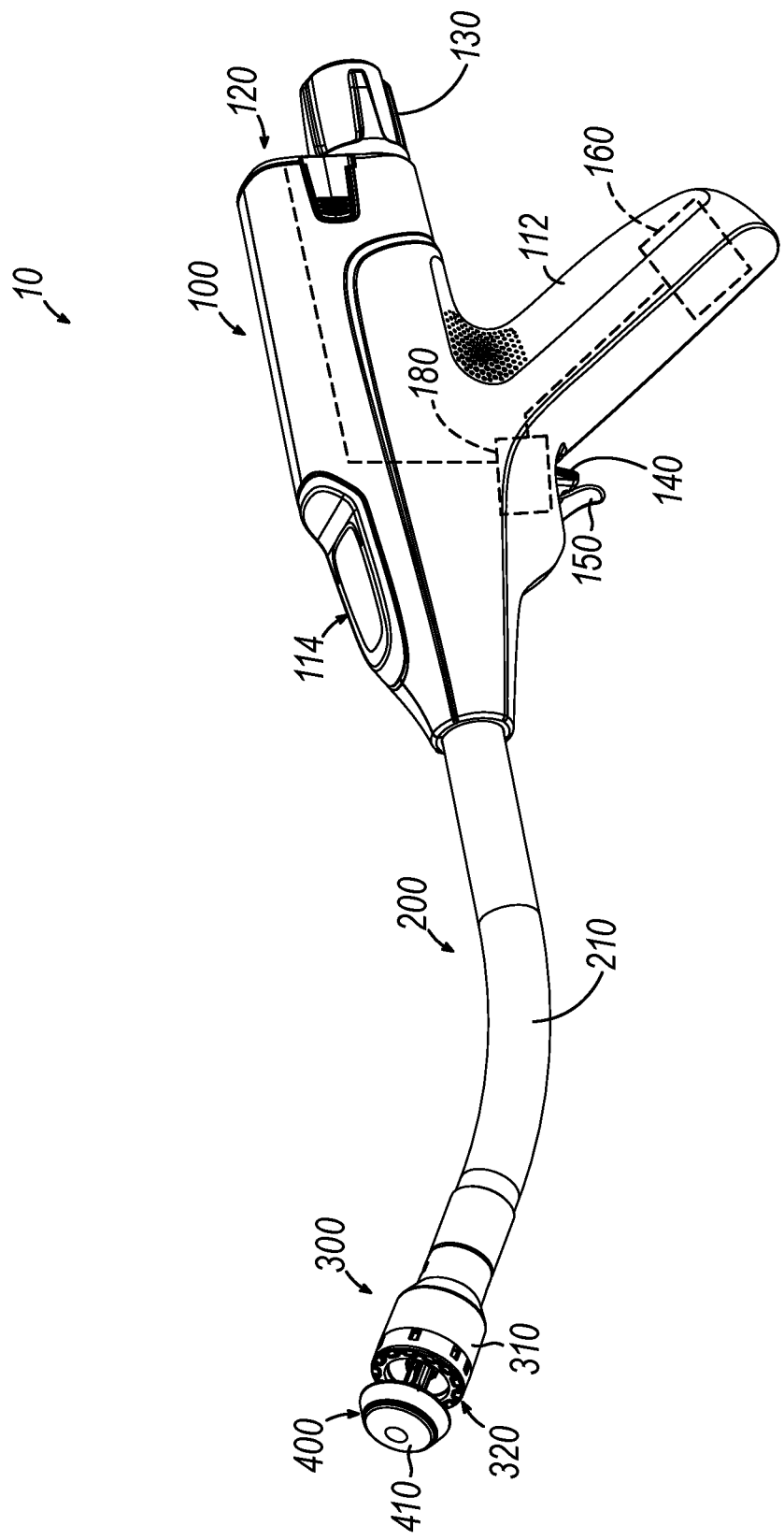
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," "clockwise," "counterclockwise," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
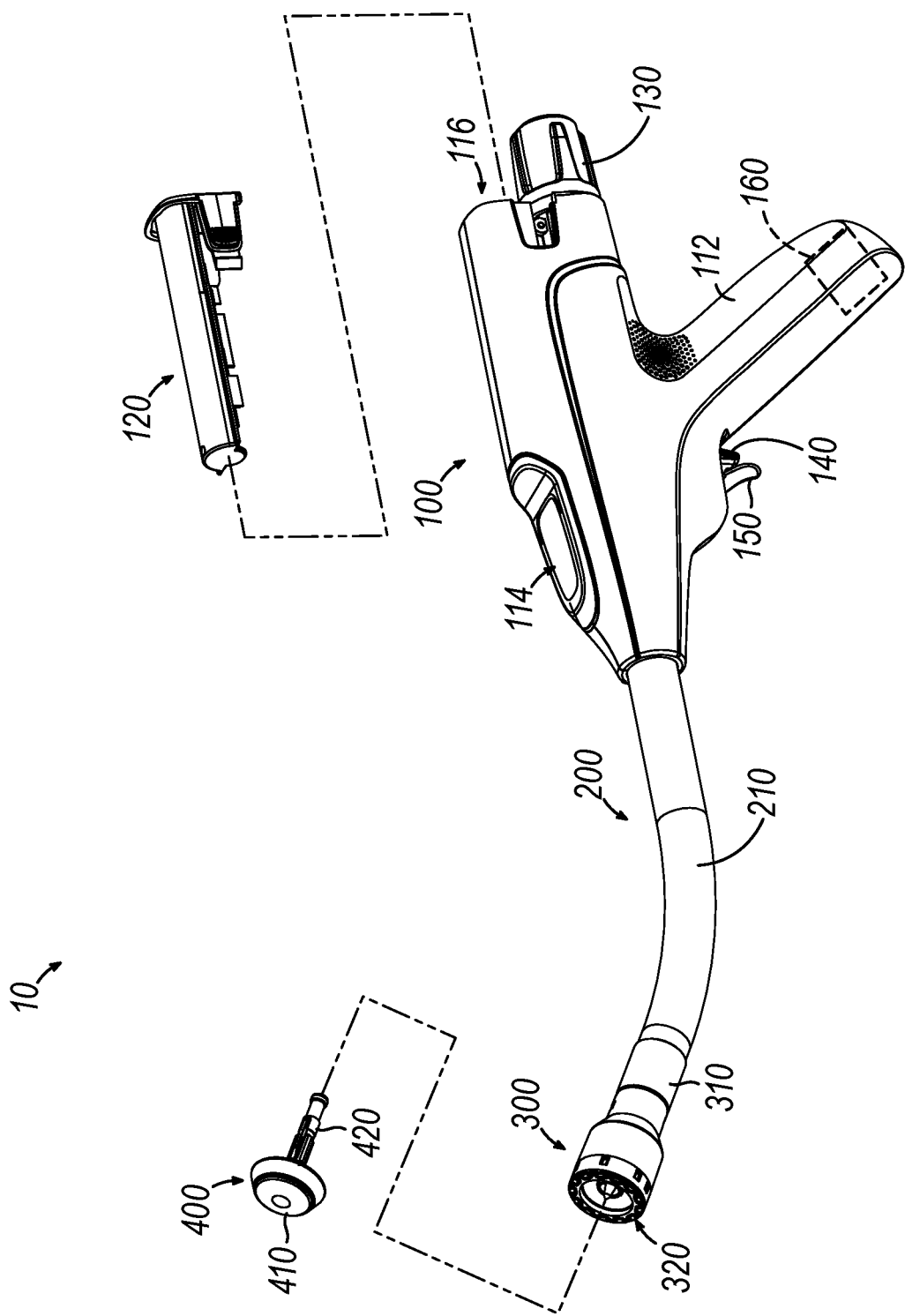
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
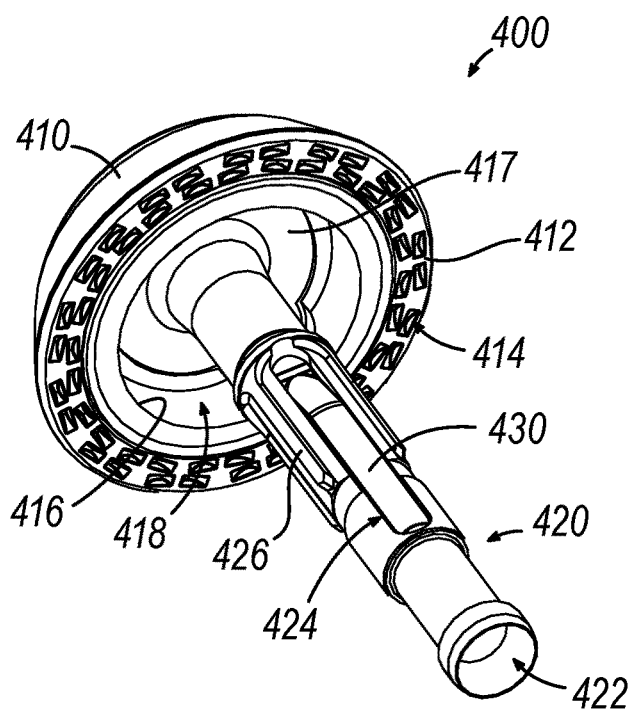
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
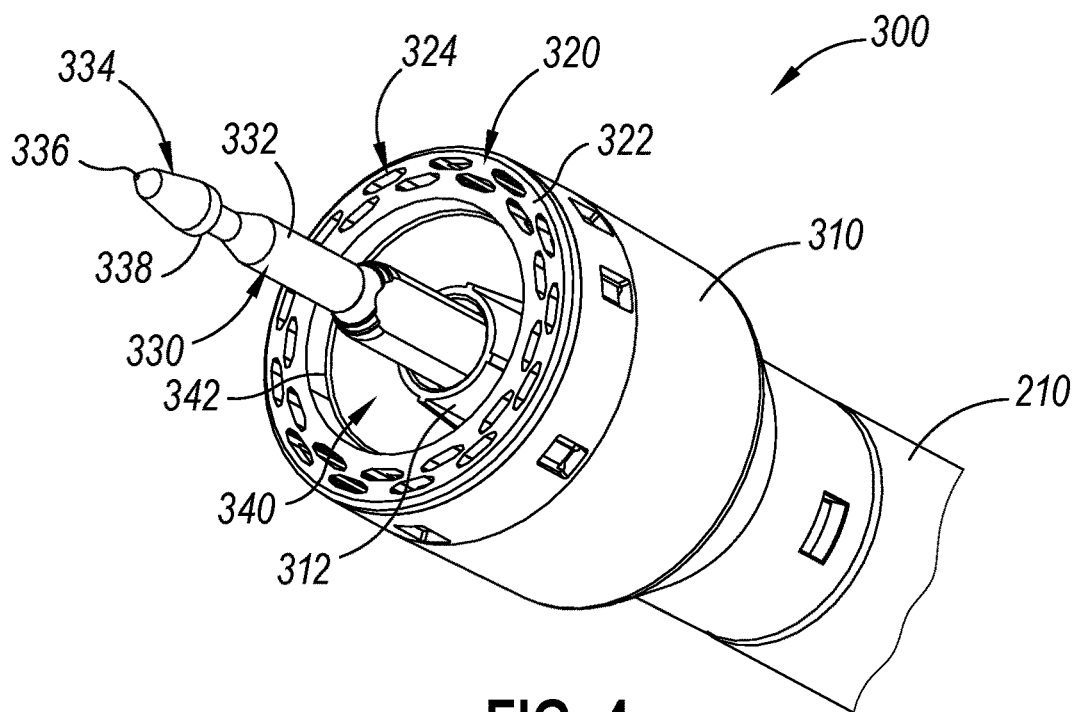
FIG. 4 depicts a perspective view of the stapling head assembly of the circular stapler of FIG. 1.
Figure 5:
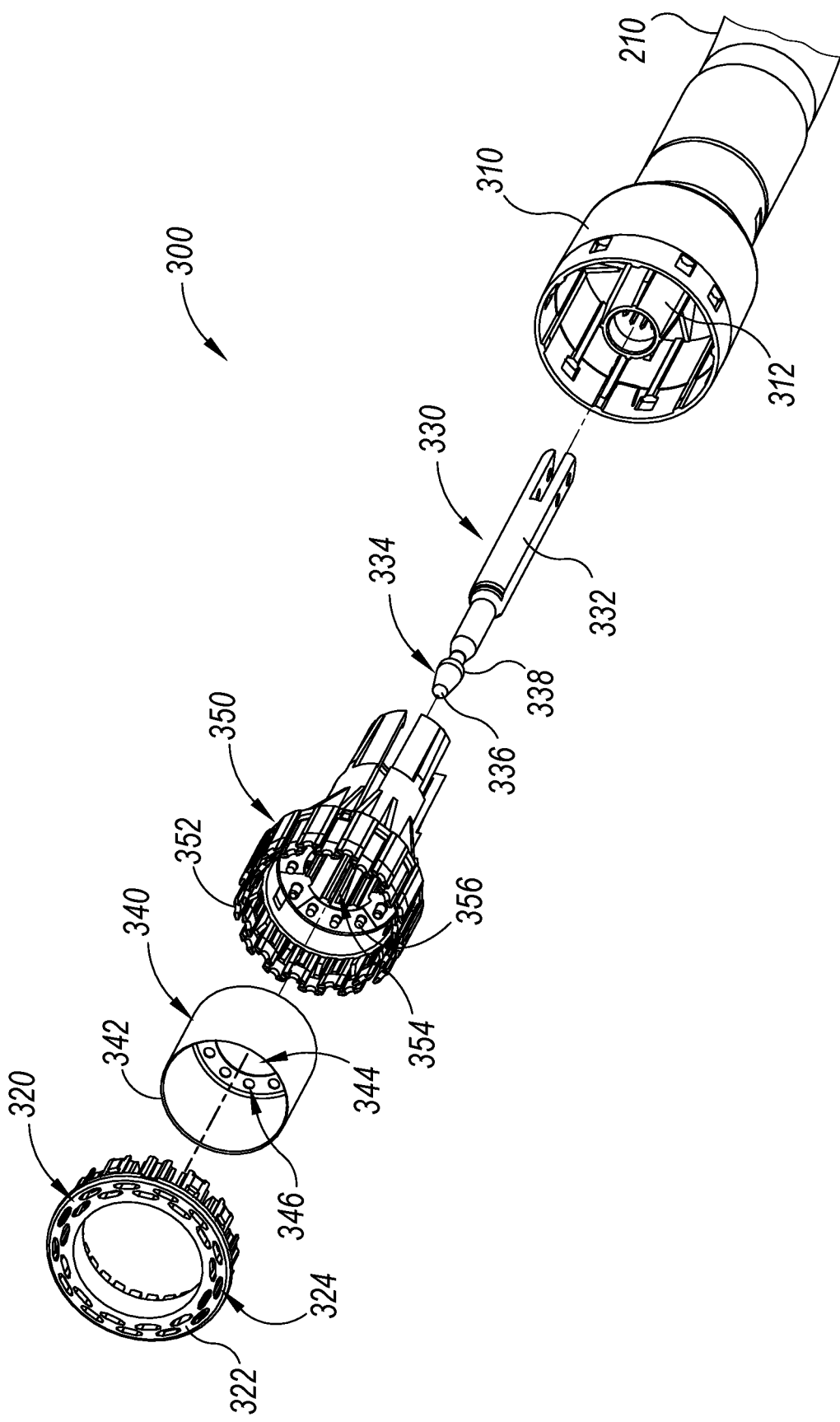
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As show best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
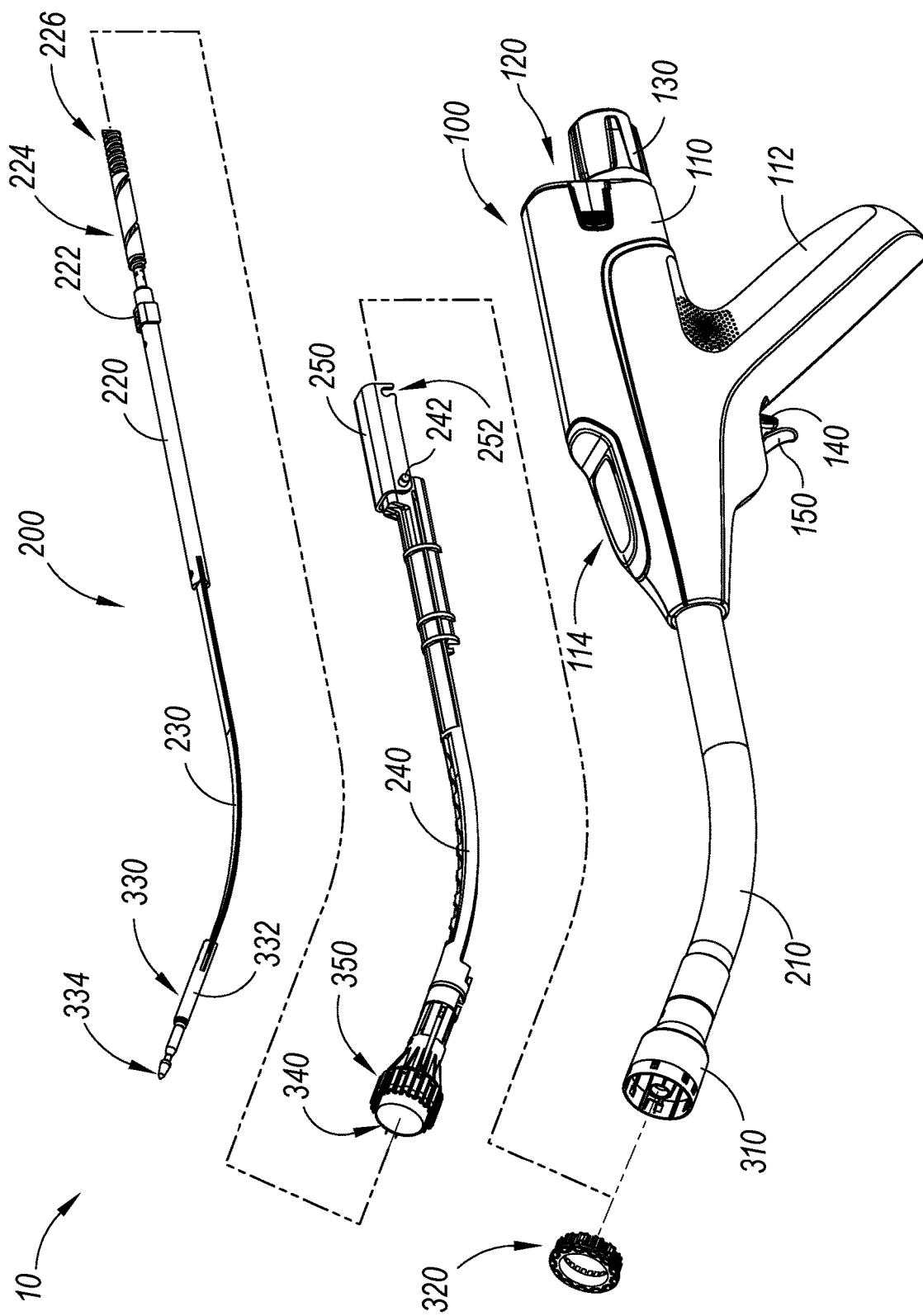
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extent anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
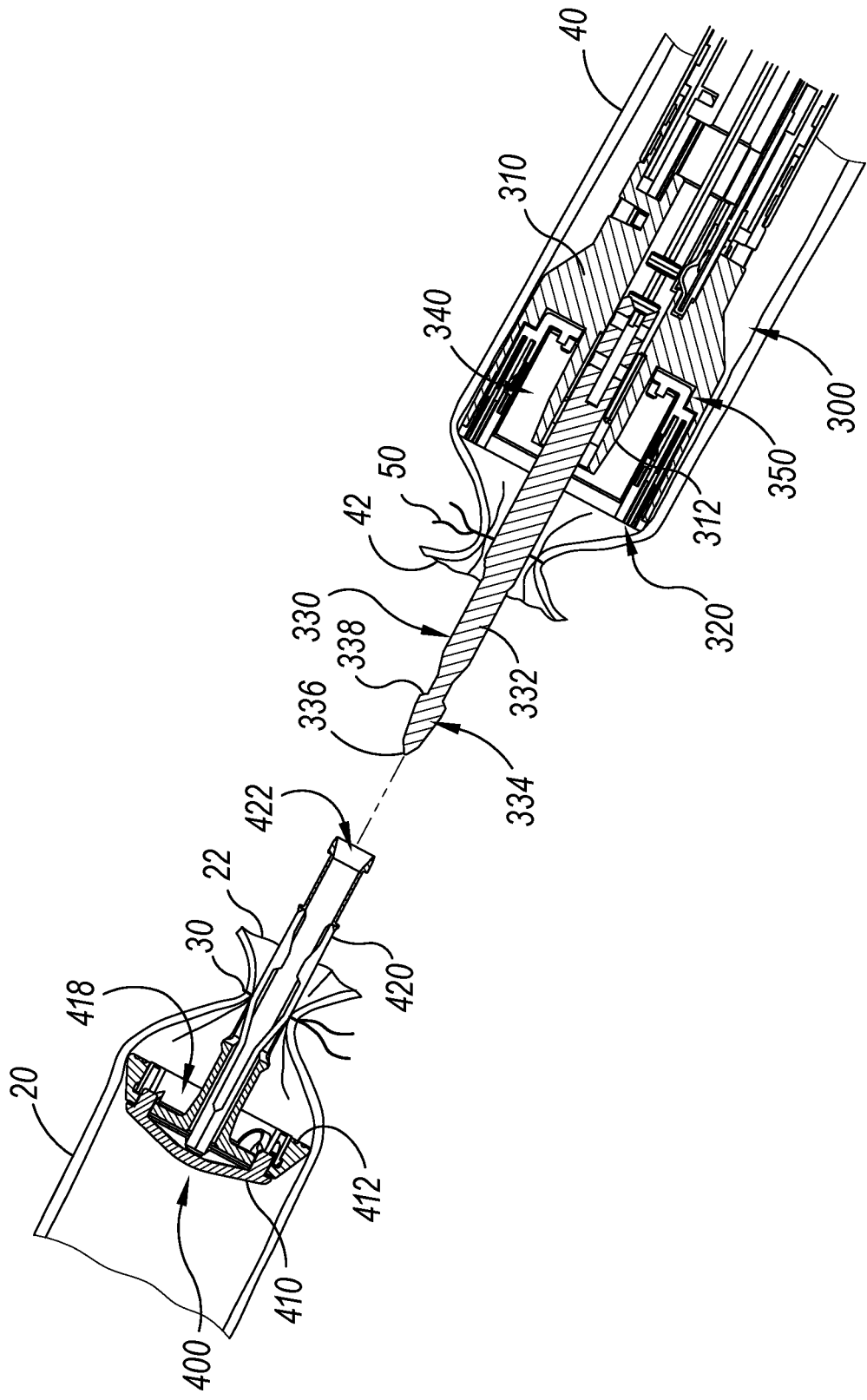
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
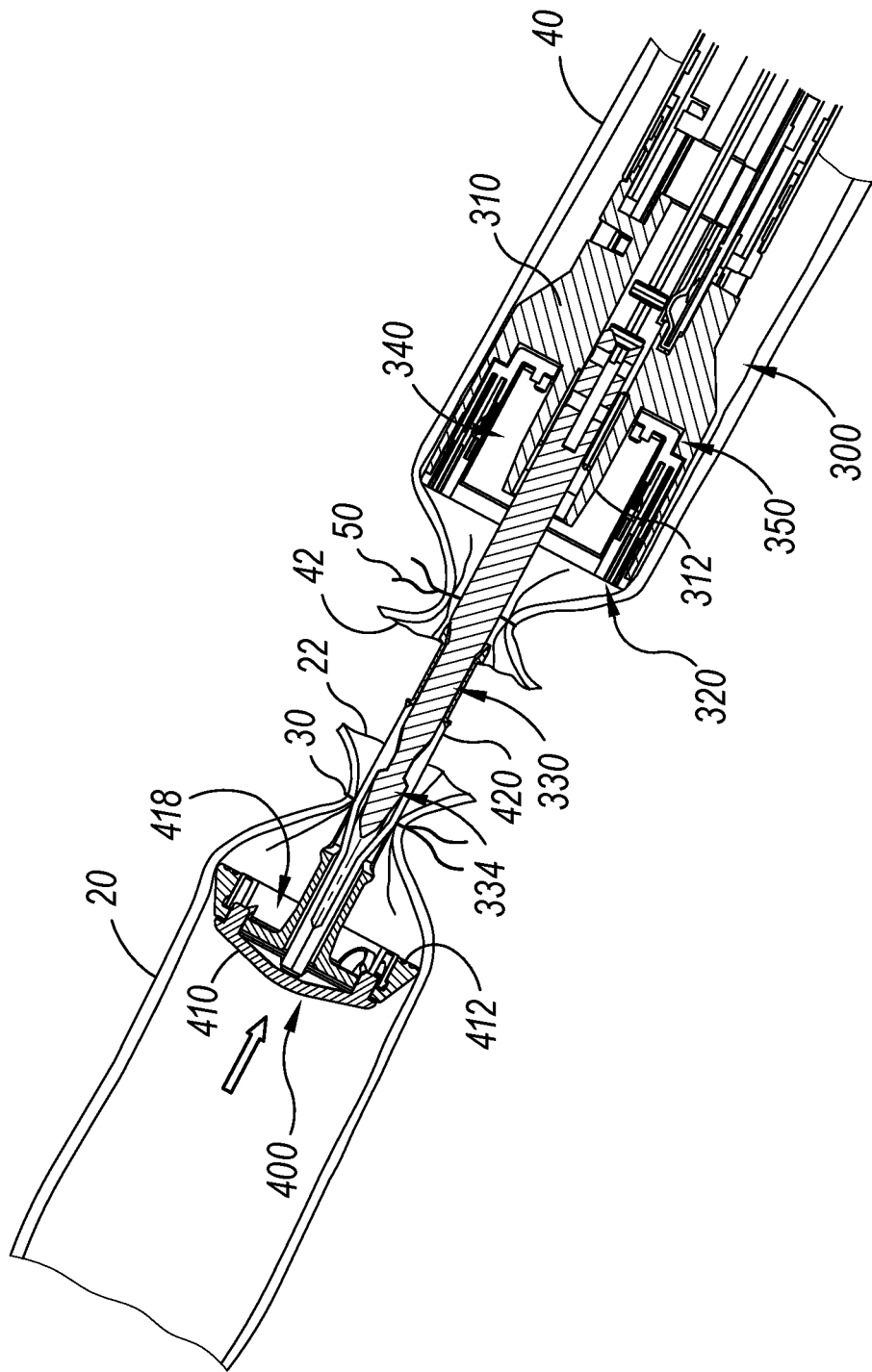
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
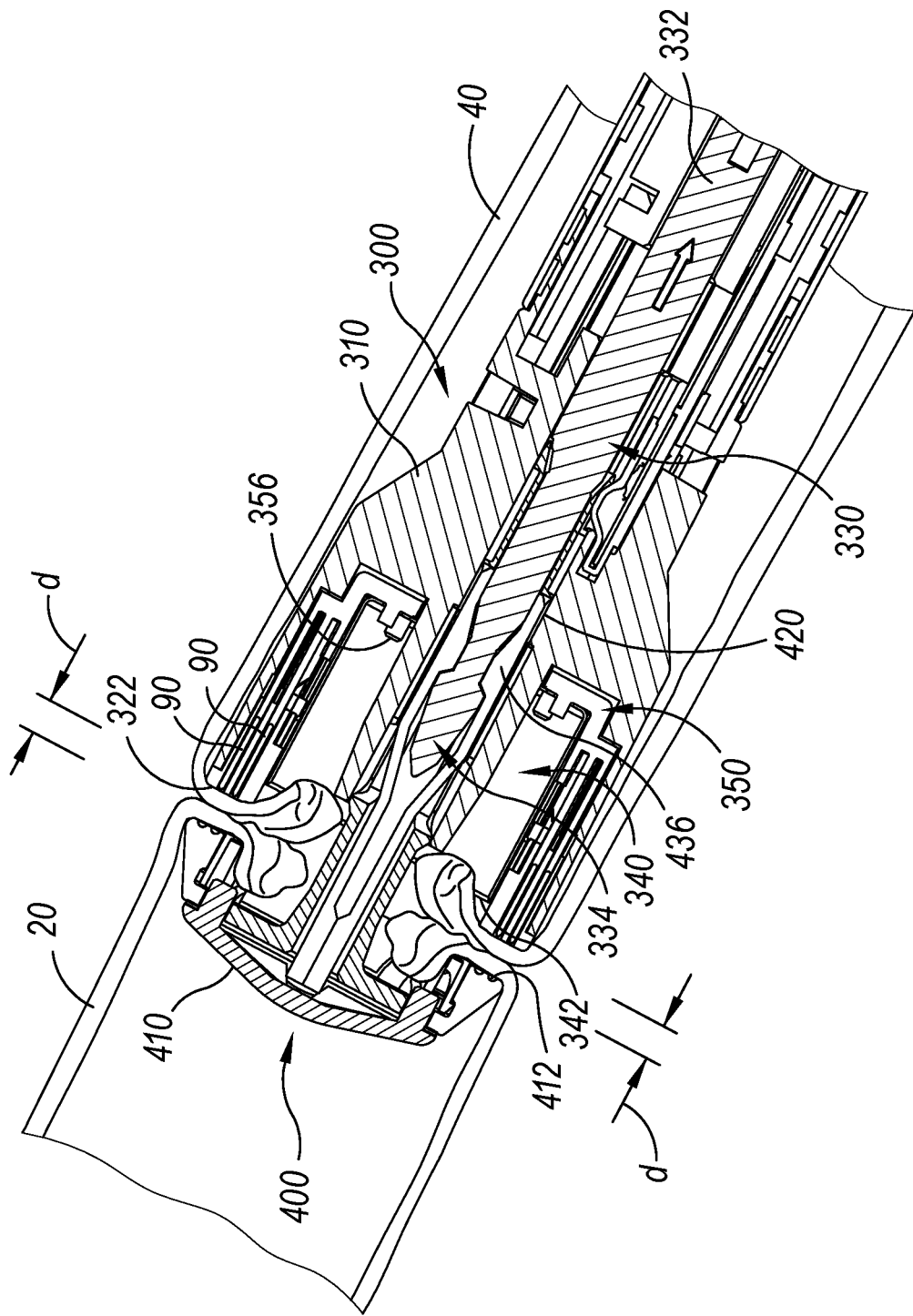
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
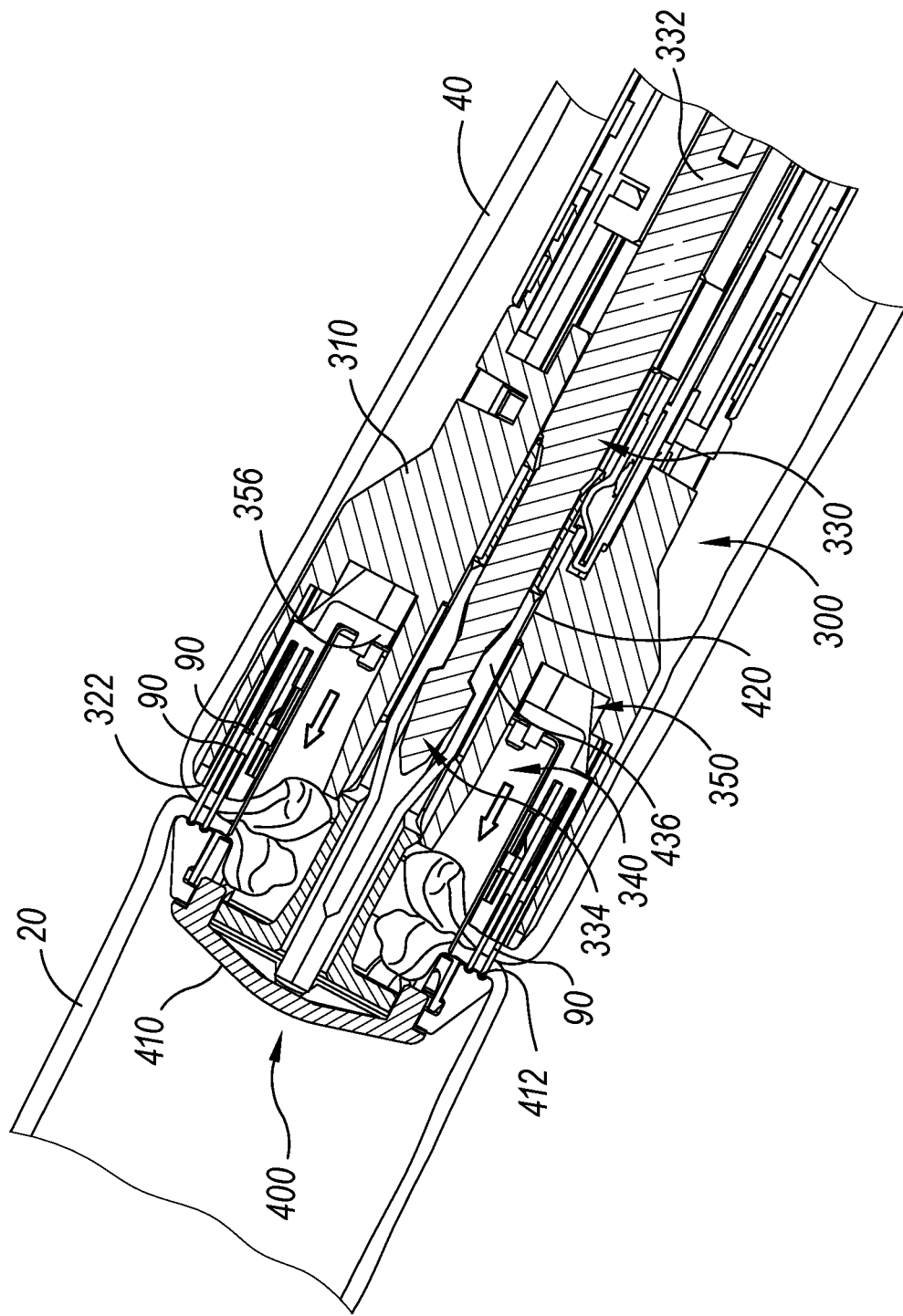
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
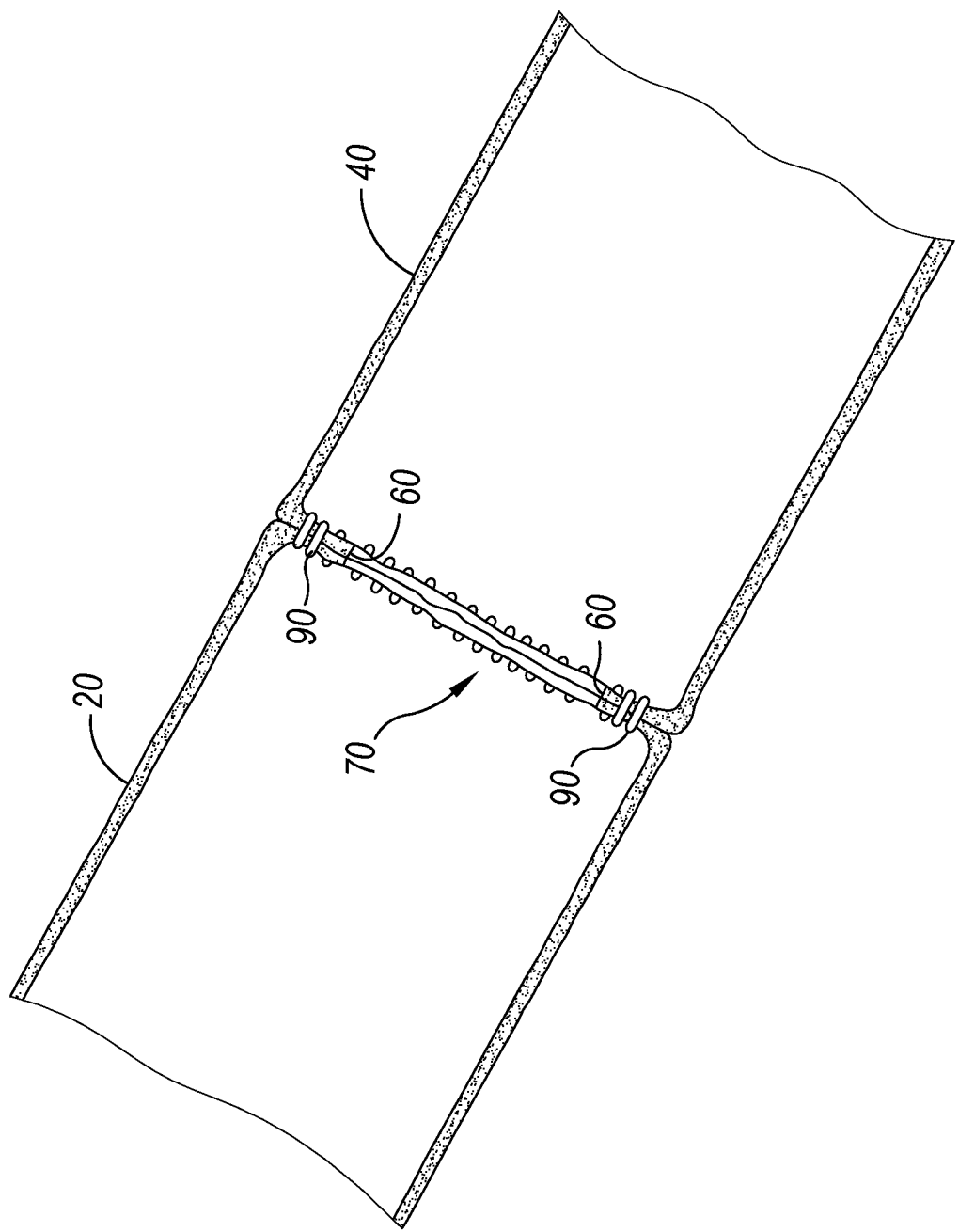
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Features for Forming Expandable Patterns of Staples

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to enable the annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and/or anvil (400) with features that enable formation of such patterns of formed staples (90). In addition, or alternatively, it may be desirable to configure stapling head assembly (300) and/or anvil (400) with features that enable increased densities of formed staples (90) while minimizing the outer diameter of anvil (400) (e.g., by maintaining the outer diameter of anvil (400) or by decreasing the outer diameter of anvil (400)). Exemplary versions of such features are described in greater detail below.

A. Exemplary Deck Member with Staple Openings in Repeating "X" Patterns

Figure 8:
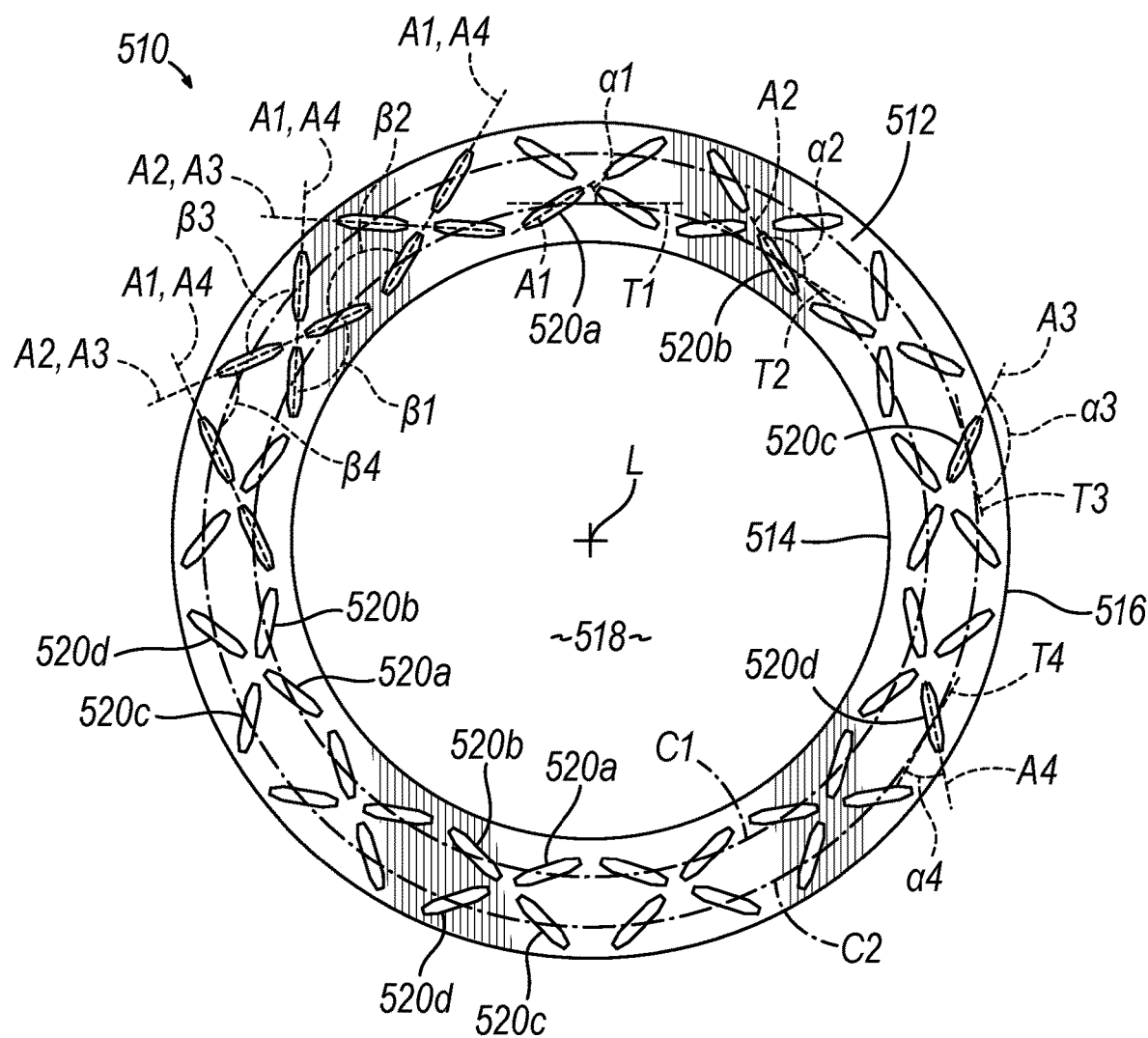
FIG. 8 depicts a top plan view of another exemplary deck member for use with the circular stapler of FIG. 1 and having two concentric annular arrays of linear staple openings arranged relative to each other in a plurality of X-shaped patterns.

FIG. 8 depicts an exemplary deck member (510) for use with instrument (10) described above. Deck member (510) is similar to deck member (320) described above except as otherwise described below. In this regard, deck member (510) may be fixedly secured to a distal end of a body member (not shown) of a stapling head assembly (not shown), such as body member (310) of stapling head assembly (300), and may be configured to permit a knife member (not shown), such as knife member (340), to translate longitudinally through deck member (510) to actuate between a proximal retracted position and a distal extended position in a manner similar to that described above in connection with FIGS. 1-7E.

As shown, deck member (510) includes a distally presented stapling surface in the form of a deck surface (512) extending radially between a generally circular radially inner edge (514) and a generally circular radially outer edge (516). Deck member (510) has a central opening (518) defined by radially inner edge (514) and having an inner diameter that is just slightly larger than the outer diameter defined by knife member (340). Deck member (510) is thus configured to permit knife member (340) to translate longitudinally through the central opening concurrently with longitudinal translation of staple driver member (350). In particular, knife member (340) is configured to actuate relative to deck member (510) between a proximal retracted position and a distal extended position, where cutting edge (342) is proximal to deck surface (512) in the proximal retracted position and distal to deck surface (512) in the distal extended position. Deck surface (512) of the present version has two concentric annular arrays of linear staple openings (520a, 520b, 520c, 520d) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (520a, 520b, 520c, 520d) is configured to slidably receive and provide a pathway for a corresponding staple driver to drive a corresponding staple (90a, 90b, 90c, 90d) (FIGS. 9A-9C) distally through deck member (510) and into a corresponding staple forming pocket when a stapling head assembly (not shown) similar to stapling head assembly (300) is actuated. In some versions, each staple opening (520a, 520b, 520c, 520d) may have a width of approximately 0.100 inch.

In the present version, staple openings (520a, 520b, 520c, 520d) are arranged in a radially inner annular array of circumferentially-alternating first and second staple openings (520a, 520b) and a radially outer annular array of circumferentially-alternating third and fourth staple openings (520c, 520d). More particularly, radially inner staple openings (520a, 520b) are arranged with uniform circumferential spacing about a longitudinal axis (L) of central opening (518), with the midpoints of each radially inner staple opening (520a, 520b) positioned at a first radial distance from longitudinal axis (L) such that the midpoints of radially inner staple openings (520a, 520b) collectively define a first reference circle (C1). As shown, each radially inner staple opening (520a, 520b) is oriented non-tangentially relative to first circle (C1). In this regard, first staple openings (520a) each extend along a respective first axis (A1) oriented at a first oblique angle ($\alpha$1) relative to a corresponding reference line (T1) that extends tangentially to first circle (C1) through the respective midpoint, and second staple openings (520b) each extend along a respective second axis (A2) oriented at a second oblique angle ($\alpha$2) relative to a corresponding reference line (T2) that extends tangentially to first circle (C1) through the respective midpoint. In the example shown, first angle ($\alpha$1) is acute such that each first staple opening (520a) extends generally radially outwardly in a clockwise direction, while second angle ($\alpha$2) is obtuse such that each second staple opening (520b) extends generally radially inwardly in a clockwise direction. In some versions, first and second angles ($\alpha$1, $\alpha$2) may be supplementary to each other. For example, first angle ($\alpha$1) may be approximately 30° and second angle ($\alpha$2) may be approximately 150°. In any event, each first staple opening (520a) and a corresponding clockwise-adjacent second staple opening (520b) may collectively define a first internal angle ($\beta$1) which opens toward inner edge (514), while each second staple opening (520b) and a corresponding clockwise-adjacent first staple opening (520a) may collectively define a second internal angle ($\beta$2) which opens toward outer edge (516).

Likewise, radially outer staple openings (520c, 520d) are arranged with uniform circumferential spacing about longitudinal axis (L) of central opening (518), with the midpoints of each radially outer staple opening (520c, 520d) positioned at a second radial distance from longitudinal axis (L) greater than the first radial distance, such that the midpoints of radially outer staple openings (520c, 520d) collectively define a second reference circle (C2) that is radially outward relative to first reference circle (C1). As shown, each radially outer staple opening (520c, 520d) is oriented non-tangentially relative to second circle (C2). In this regard, third staple openings (520c) each extend along a respective third axis (A3) oriented at a third oblique angle ($\alpha$3) relative to a corresponding reference line (T3) that extends tangentially to second circle (C2) through the respective midpoint, and fourth staple openings (520d) each extend along a respective fourth axis (A4) oriented at a fourth oblique angle ($\alpha$4) relative to a corresponding reference line (T4) that extends tangentially to second circle (C2) through the respective midpoint. In the example shown, third angle ($\alpha$3) is obtuse such that each third staple opening (520c) extends generally radially inwardly in a clockwise direction, while fourth angle ($\alpha$4) is acute such that each fourth staple opening (520d) extends generally radially outwardly in a clockwise direction. In some versions, third and fourth angles ($\alpha$3, $\alpha$4) may be supplementary to each other. For example, third angle ($\alpha$3) may be approximately 150° and fourth angle ($\alpha$4) may be approximately 30°. In any event, each third staple opening (520c) and a corresponding clockwise-adjacent fourth staple opening (520d) may collectively define a third internal angle ($\beta$3) which opens toward outer edge (516), while each fourth staple opening (520d) and a corresponding clockwise-adjacent third staple opening (520c) may collectively define a fourth internal angle ($\beta$4) which opens toward inner edge (514).

In the example shown, radially inner staple openings (520a, 520b) are each generally aligned with a corresponding radially outer staple opening (520c, 520d) along their respective axes (A1, A2, A3, A4). More particularly, first staple openings (520a) are each generally aligned with a corresponding fourth staple opening (520d) along their respective first and fourth axes (A1, A4), and second staple openings (520b) are each generally aligned with a corresponding third staple opening (520c) along their respective second and third axes (A2, A3). For example, the first axis (A1) of a first staple opening (520a) may be colinear with the fourth axis (A4) of the corresponding axially-aligned fourth staple opening (520d), and the second axis (A2) of a second staple opening (520b) may be colinear with the third axis (A3) of the corresponding axially-aligned third staple opening (520c). In this regard, first angle ($\alpha$1) may be substantially equal to fourth angle ($\alpha$4), and second angle ($\alpha$2) may be substantially equal to third angle ($\alpha$3).

In the example shown, radially inner staple openings (520a, 520b) are also each generally aligned with a corresponding radially outer staple opening (520c, 520d) in a radial direction. More particularly, first staple openings (520a) are each generally aligned with a corresponding third staple opening (520c) in a radial direction, and second staple openings (520b) are each generally aligned with a corresponding fourth staple opening (520d) in a radial direction.

Due to the relative positions and orientations of staple openings (520a, 520b, 520c, 520d), the annular arrays of staple openings (520a, 520b, 520c, 520d) may define a plurality of cross-shaped staple opening patterns and, more particularly, X-shaped staple opening patterns. In this regard, each first staple opening (520a), corresponding clockwise-adjacent second staple opening (520b), corresponding radially-aligned third staple opening (520c), and corresponding axially-aligned fourth staple opening (520d) may collectively define a respective X-shaped staple opening pattern. More particularly, the colinear first and fourth axes (A1, A4) of such first and fourth staple openings (520a, 520d) may intersect with the colinear second and third axes (A2, A3) of such second and third staple openings (520b, 520c) at a location between such staple openings (520a, 520b, 520c, 520d). In the example shown, the width of each X-shaped staple opening pattern in the circumferential direction is greater than the distance between adjacent pairs of X-shaped staple opening patterns in the circumferential direction. In some versions, the crossing point of each X-shaped staple opening pattern (e.g., the intersection between the corresponding colinear first and fourth axes (A1, A4) and the corresponding colinear second and third staple openings (520b, 520c)) may be offset from (e.g., radially outward of) a circumferential midline between inner and outer edges (514, 516) such that the crossing points are positioned closer to outer edge (516) than inner edge (514). In addition, or alternatively, the lengths of the radially inner staple openings (520a, 520b) may be greater than the lengths of the radially outer staple openings (520c, 520d). In any event, the X-shaped staple opening patterns may enable the annular arrays of formed staples (90a, 90b, 90c, 90d) driven from deck member (510) to expand radially while maintaining a secure seal as described in greater detail below.

Figure 9A:
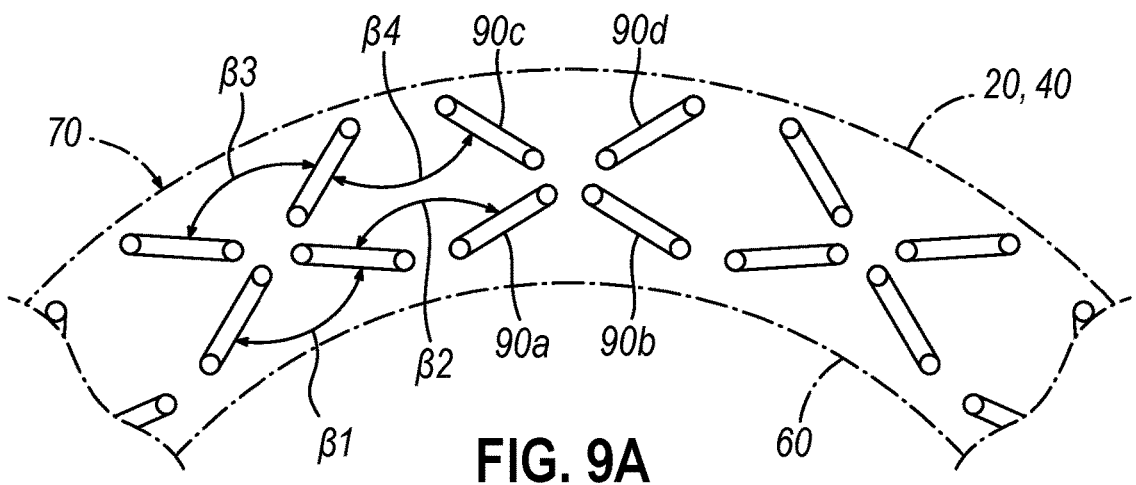
FIG. 9A depicts a partial top plan view of two concentric annular arrays of staples driven from the deck member of FIG. 8, showing the annular arrays of staples in a radially unexpanded state.
Figure 9B:
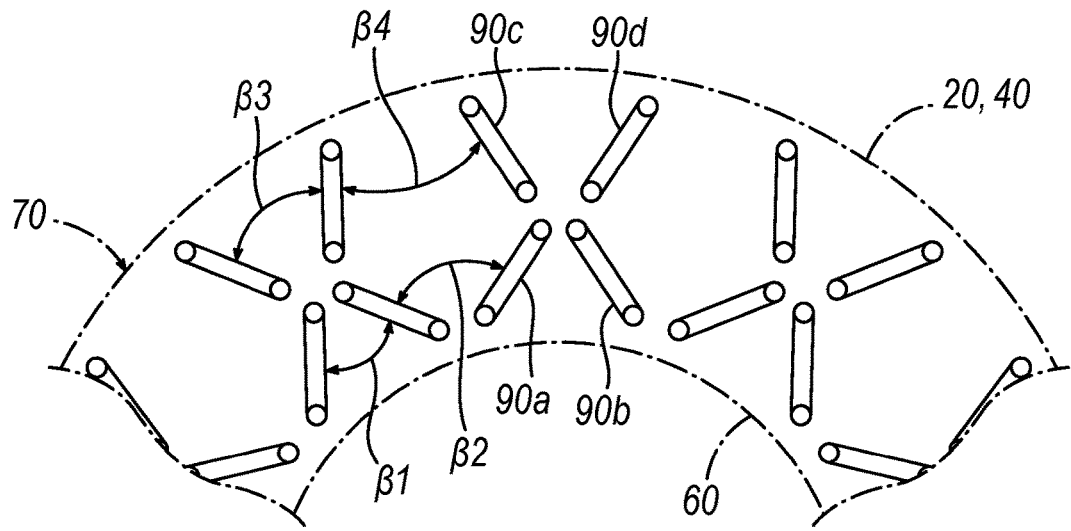
FIG. 9B depicts a partial top plan view of the annular arrays of staples of FIG. 9A, showing the annular arrays of staples in a first radially expanded state.
Figure 9C:
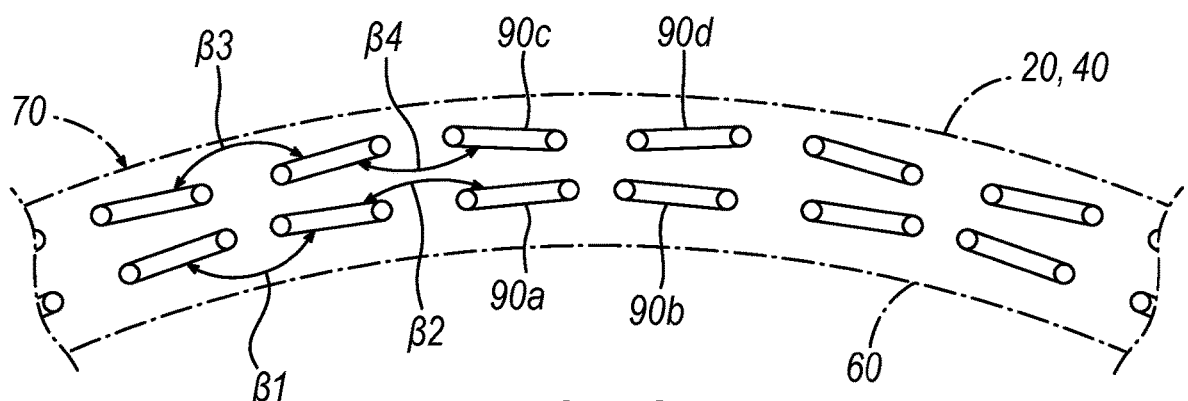
FIG. 9C depicts a partial top plan view of the annular arrays of staples of FIG. 9A, showing the annular arrays of staples in a second radially expanded state.

Referring now to FIGS. 9A-9C, the annular arrays of formed staples (90a, 90b, 90c, 90d) driven from deck member (510) to secure tubular anatomical structures (20, 40) at anastomosis (70) may define a plurality of X-shaped staple patterns corresponding to the X-shaped staple opening patterns defined by the annular arrays of staple openings (520a, 520b, 520c, 520d). In this regard, formed staples (90a, 90b, 90c, 90d) may initially be positioned and oriented in manners corresponding to the respective staple openings (520a, 520b, 520c, 520d) so as to define the same internal angles (β1, β2, β3, β4) while anastomosis (70) is maintained in a radially unexpanded state, as shown in FIG. 9A. Formed staples (90a, 90b, 90c, 90d) may each be reoriented to accommodate expansion of at least a portion of anastomosis (70) (e.g., the inner diameter of the anastomosis (70) defined by the severed edge (60)) to one or more radially expanded states without stretching the puncture openings in tubular anatomical structures (20, 40) through which formed staples (90a, 90b, 90c, 90d) extend, as shown in FIGS. 9B and 9C. For example, formed staples (90a, 90b, 90c, 90d) may each be generally pivoted about their respective radially inner and/or outer ends such that first and second formed staples (90a, 90b) are rotated toward each other, thereby decreasing the first and second internal angles (β1, β2), and such that third and fourth formed staples (90c, 90d) are rotated toward each other, thereby decreasing the third and fourth internal angles (β3, β4), to accommodate expansion of anastomosis (70) in a first radial direction to a first radially expanded state (FIG. 9B). Similarly, formed staples (90a, 90b, 90c, 90d) may each be generally pivoted about their respective radially inner and/or outer ends such that first and second formed staples (90a, 90b) are rotated away from each other, thereby increasing the first and second internal angles (β1, β2), and such that third and fourth formed staples (90c, 90d) are rotated away from each other, thereby increasing the third and fourth internal angles (β3, β4), to accommodate expansion of anastomosis (70) in a second radial direction to a second radially expanded state (FIG. 9C).

B. Exemplary Deck Member with X-Shaped Staple Openings in Uniform Orientations

Figure 10:
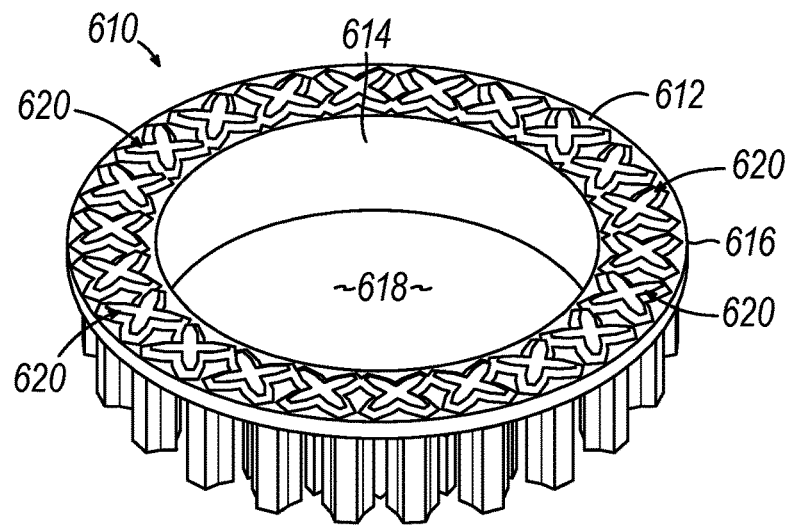
FIG. 10 depicts a top perspective view of another exemplary deck member for use with the circular stapler of FIG. 1 and having a single annular array of X-shaped staple openings having uniform orientations.
Figure 11:
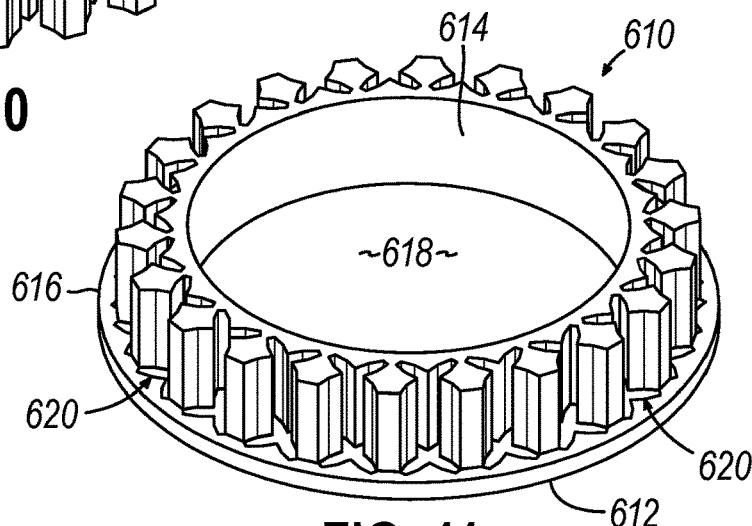
FIG. 11 depicts a bottom perspective view of the deck member of FIG. 10.
Figure 12:
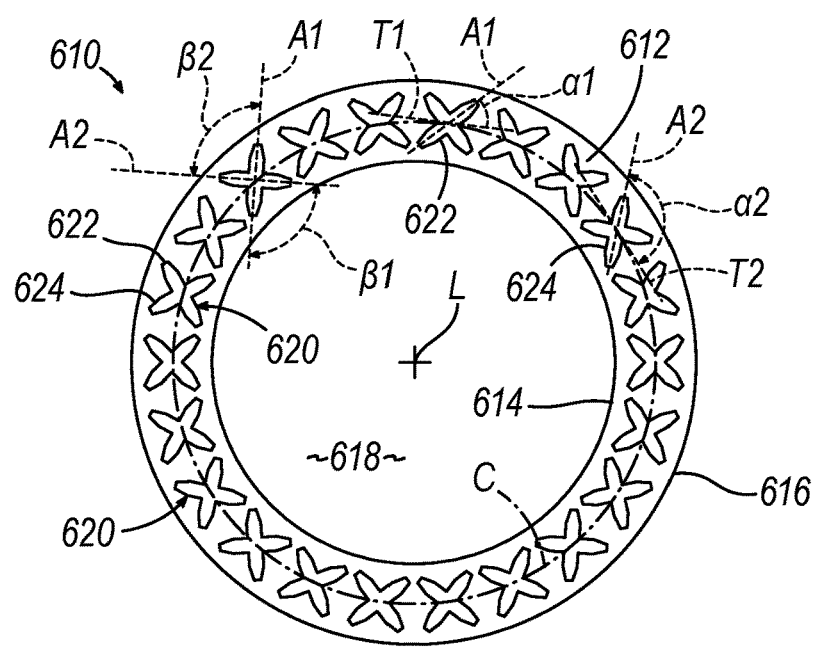
FIG. 12 depicts a top plan view of the deck member of FIG. 10.

FIGS. 10-12 depict an exemplary deck member (610) for use with instrument (10) described above. Deck member (610) is similar to deck member (320) described above except as otherwise described below. In this regard, deck member (610) may be fixedly secured to a distal end of a body member (not shown) of a stapling head assembly (not shown), such as body member (310) of stapling head assembly (300), and may be configured to permit a knife member (not shown), such as knife member (340), to translate longitudinally through deck member (610) to actuate between a proximal retracted position and a distal extended position in a manner similar to that described above in connection with FIGS. 1-7E.

As shown, deck member (610) includes a distally presented stapling surface in the form of a deck surface (612) extending radially between a generally circular radially inner edge (614) and a generally circular radially outer edge (616). Deck member (610) has a central opening (618) defined by radially inner edge (614) and having an inner diameter that is just slightly larger than the outer diameter defined by knife member (340). Deck member (610) is thus configured to permit knife member (340) to translate longitudinally through the central opening concurrently with longitudinal translation of staple driver member (350). In particular, knife member (340) is configured to actuate relative to deck member (610) between a proximal retracted position and a distal extended position, where cutting edge (342) is proximal to deck surface (612) in the proximal retracted position and distal to deck surface (612) in the distal extended position.

Deck surface (612) of the present version has a single annular array of X-shaped staple openings (620) arranged to align with corresponding arrays of X-shaped staple drivers (not shown) such as X-shaped staple driver assemblies (830) described below, and with corresponding arrays of staple forming pockets (not shown) similar to staple forming pockets (414) of anvil (400) described above. Each staple opening (620) is configured to slidably receive and provide a pathway for a corresponding staple driver to drive a corresponding staple assembly (640) (FIGS. 13-14) distally through deck member (610) and into a corresponding staple forming pocket when a stapling head assembly (not shown) similar to stapling head assembly (300) is actuated. In the example shown, each staple opening (620) includes overlapping first and second linear staple opening portions (622, 624) which are oriented perpendicularly to each other, and which intersect each other at or near their respective midpoints to define a crossing point of the respective staple opening (620).

In the present version, staple openings (620) are arranged with uniform circumferential spacing about a longitudinal axis (L) of central opening (618), with the midpoints of each staple opening portion (622, 624) (and thus the crossing points of each staple opening (620)) positioned at a same radial distance from longitudinal axis (L) such that the midpoints of each staple opening portion (622, 624) (and thus the crossing points of staple openings (620)) collectively define a reference circle (C). As shown, each staple opening portion (622, 624) is oriented non-tangentially relative to circle (C). In this regard, first staple opening portions (622) each extend along a respective first axis (A1) oriented at a first oblique angle (α1) relative to a corresponding reference line (T1) that extends tangentially to circle (C) through the respective midpoint, and second staple opening portions (624) each extend along a respective second axis (A2) oriented at a second oblique angle (α2) relative to a corresponding reference line (T2) that extends tangentially to circle (C) through the respective midpoint. In the example shown, first angle (α1) is acute such that each first staple opening portion (622) extends generally radially outwardly in a clockwise direction, while second angle (α2) is obtuse such that each second staple opening portion (624) extends generally radially inwardly in a clockwise direction. In some versions, first and second angles (α1, α2) may be supplementary to each other. For example, first angle (α1) may be approximately 45° and second angle (α2) may be approximately 135°. In any event, each first staple opening portion (622) and corresponding second staple opening portion (624) may collectively define a first internal angle (β1) which opens toward inner edge (614) and a second internal angle (β2) which opens toward outer edge (616).

In the example shown, the width of each X-shaped staple opening (620) in the circumferential direction is greater than the distance between adjacent pairs of X-shaped staple openings (620) in the circumferential direction. In some versions, the crossing point of each X-shaped staple opening (620) may be offset from (e.g., radially outward of) a circumferential midline between inner and outer edges (614, 616) such that the crossing points are positioned closer to outer edge (616) than inner edge (614). In addition, or alternatively, the lengths of the portions of staple openings (620) that are radially inward of the crossing points may be greater than the lengths of the portions of staple openings (620) that are radially outward of the crossing points. In any event, the X-shaped staple openings (620) may enable the annular array of formed staple assemblies (640) driven from deck member (610) to expand radially while maintaining a secure seal as described in greater detail below.

Figure 13:
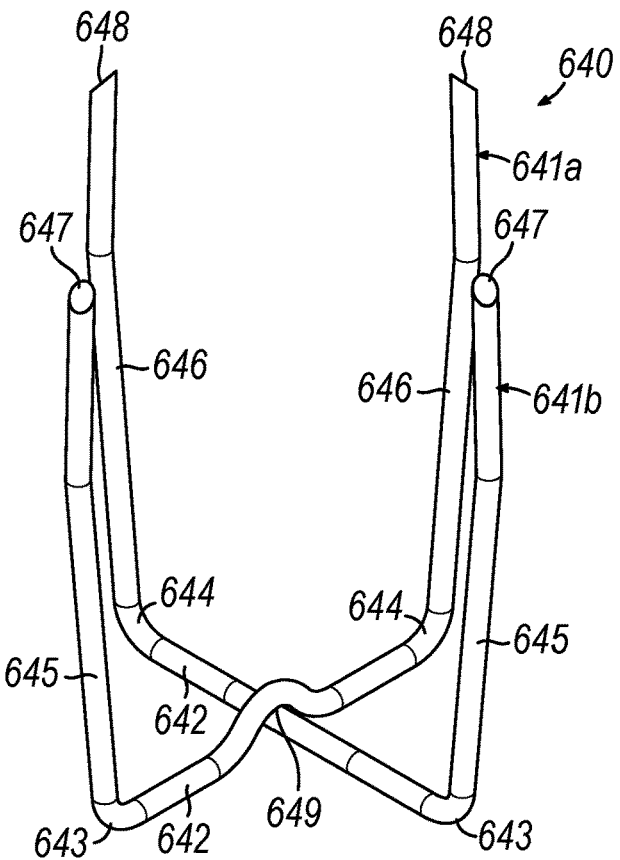
FIG. 13 depicts a top perspective view of an X-shaped staple assembly for use with the deck member of FIG. 10, showing the staple assembly in an initial state.
Figure 14:
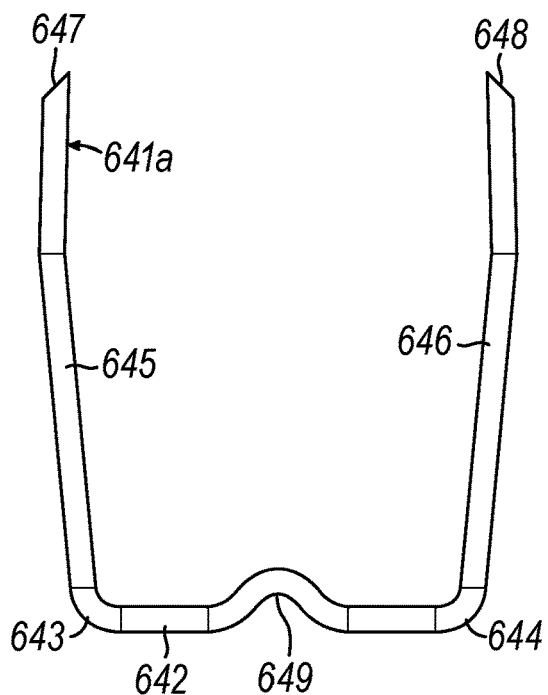
FIG. 14 depicts a side elevational view of a first staple of the staple assembly of FIG. 13.

Referring now to FIGS. 13-14, each X-shaped staple assembly (640) of the present example includes a first staple (641*a*) and a second staple (641*b*). As shown, each staple (641*a*, 641*b*) includes a crown (642) extending between first and second ends (643, 644), and further includes first and second legs (645, 646) extending upwardly and generally perpendicularly from respective ends (643, 644) of crown (642) to respective sharp tips (647, 648) configured to puncture tissue, such as tubular anatomical structures (20, 40). In the example shown, the first and second staples (641*a*, 641*b*) of each staple assembly (640) overlap each other at or near the corresponding midpoints of the respective crowns (642). In this regard, the crown (642) of each first staple (641*a*) is upwardly bent at or near the midpoint thereof to define a recess (649) for receiving the crown (642) of the corresponding overlapping second staple (641*b*) such that each first staple (641*a*) may be seated on the corresponding second staple (641*b*). In some versions, the recess (649) of each first staple (641*a*) may be configured to pivotably receive the crown (642) of the corresponding second staple (641*b*) to permit relative pivoting of first and second staples (641*a*, 641*b*) about their respective midpoints (e.g., the midpoints of their respective crowns (642)).

Figure 15A:
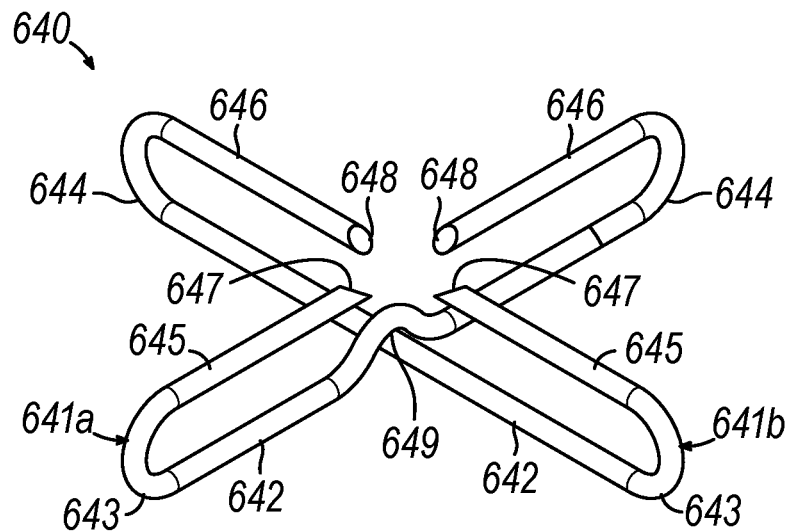
FIG. 15A depicts a top perspective view of the staple assembly of FIG. 13 in a two-dimensional formed state.
Figure 15B:
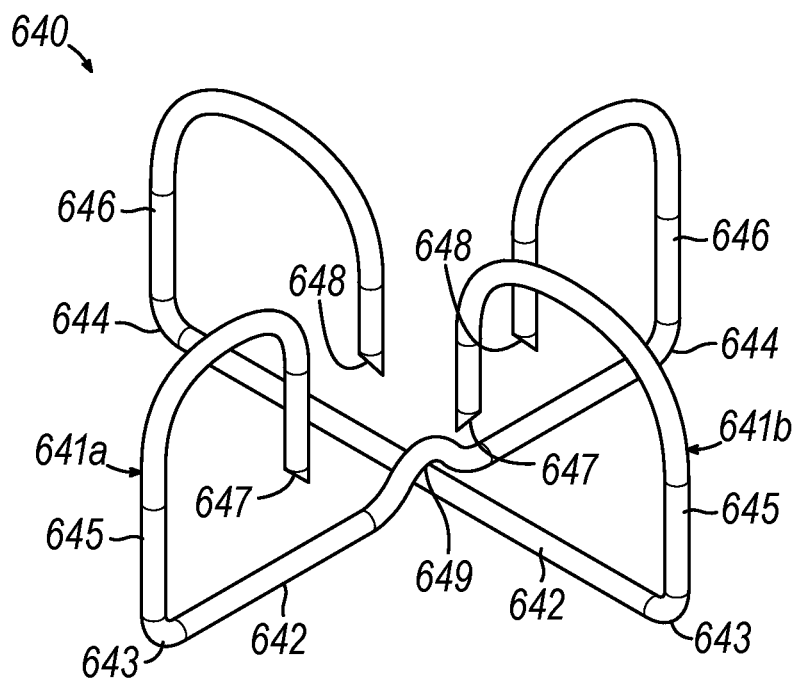
FIG. 15B depicts a top perspective view of the staple assembly of FIG. 13 in a three-dimensional formed state.

As shown in FIGS. 15A-15B, each staple assembly (640) may be formed by a corresponding staple forming pocket into either a two-dimensional formed state (FIG. 15A) or a three-dimensional formed state (FIG. 15B). In the two-dimensional formed state shown in FIG. 15A, the crown (642) and bent legs (645, 646) of each staple (641*a*, 641*b*) each reside in a corresponding plane, such that the tips (647, 648) of each staple (641*a*, 641*b*) confront each other within the corresponding plane. In this regard, legs (645, 646) of each staple (641*a*, 641*b*) may have lengths that are sufficiently short to prevent the corresponding tips (647, 648) from colliding with each other when staple assembly (640) is in the two-dimensional formed state. In the three-dimensional formed state shown in FIG. 15B, the bent legs (645, 646) of each staple (641*a*, 641*b*) are deflected off-plane from the corresponding crown (642). Bent legs (645, 646) may have non-uniform lengths to provide a three-dimensional pressure gradient in a radially outward direction (e.g., from a tightest point to a loosest point) to ensure proper healing conditions and a secure seal. In some versions, the three-dimensional formed state of staples (641*a*, 641*b*) may be provided in accordance with one or more teachings of U.S. Pub. No. 2018/0132849, entitled "Staple Forming Pocket Configurations for Circular Surgical Stapler Anvil," published May 17, 2018, incorporated by reference above, and/or U.S. Pub. No. 2020/0038017, entitled "Surgical End Effectors with Staple Cartridges," published Feb. 6, 2020, the disclosure of which is incorporated by reference herein.

Figure 16A:
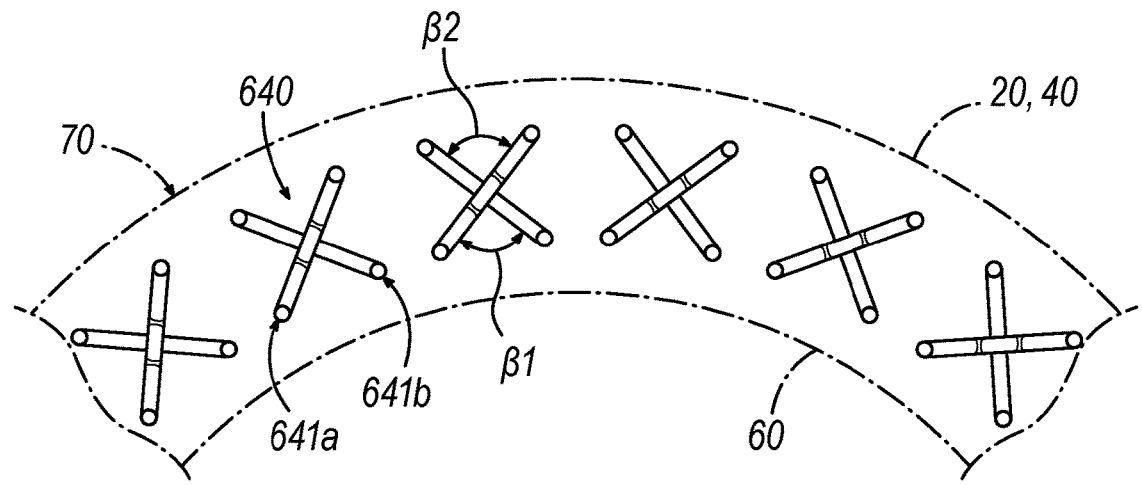
FIG. 16A depicts a partial top plan view of an annular array of X-shaped staple assemblies driven from the deck member of FIG. 10, showing the annular array of staple assemblies in a radially unexpanded state.
Figure 16B:
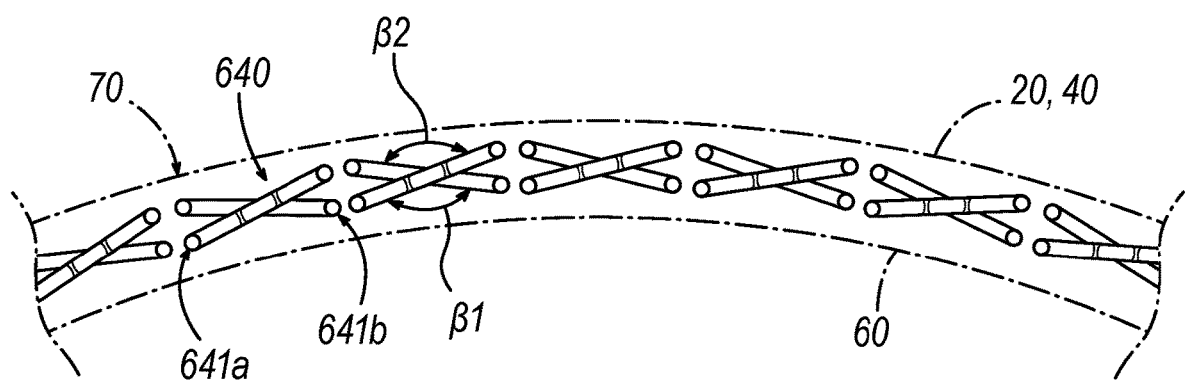
FIG. 16B depicts a partial top plan view of the annular array of staple assemblies of FIG. 16A, showing the annular array of staple assemblies in a radially expanded state.

Referring now to FIGS. 16A-16B, the annular arrays of formed staple assemblies (640) driven from deck member (610) to secure tubular anatomical structures (20, 40) at anastomosis (70) may define a plurality of X-shaped staple patterns corresponding to X-shaped staple openings (620). In this regard, staples (641*a*, 641*b*) of formed staple assemblies (640) may initially be positioned and oriented in manners corresponding to the respective staple opening portions (622, 624) so as to define the same internal angles ($\beta 1$, $\beta 2$) while anastomosis (70) is maintained in an unexpanded state, as shown in FIG. 16A. Formed staples (641*a*, 641*b*) may each be reoriented to accommodate expansion of at least a portion of anastomosis (70) (e.g., the inner diameter of the anastomosis (70) defined by the severed edge (60)) to one or more expanded states without stretching the puncture openings in tubular anatomical structures (20, 40) through which formed staples (641*a*, 641*b*) extend, as shown in FIG. 16B. For example, formed staples (641*a*, 641*b*) may each be generally pivoted about their respective radially inner and/or outer ends such that their respective radially inner ends are rotated away from each other and their respective radially outer ends are rotated toward each other, thereby increasing the first and second internal angles ($\beta 1$, $\beta 2$), to accommodate expansion of anastomosis (70) in a first radial direction to a first expanded state (FIG. 16B). Similarly, formed staples (641*a*, 641*b*) may each be generally pivoted about their respective radially inner and/or outer ends such that their respective radially inner ends are rotated toward each other and their respective radially outer ends are rotated toward each other, thereby decreasing the first and second internal angles ($\beta 1$, $\beta 2$), to accommodate expansion of anastomosis (70) in a second radial direction to a second expanded state (not shown).

Figure 17:
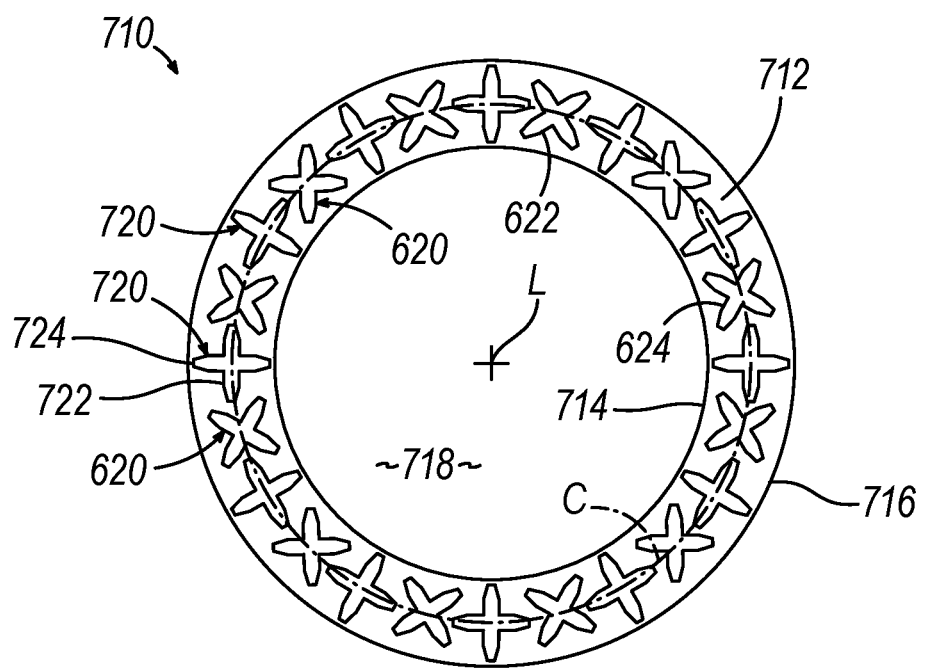
FIG. 17 depicts a top plan view of another exemplary deck member for use with the circular stapler of FIG. 1 and having a single annular array of X-shaped staple openings having alternating orientations.

C. Exemplary Deck Member with X-Shaped Staple Openings in Alternating Orientations FIG. 17 depicts an exemplary deck member (710) for use with instrument (10) described above. Deck member (710) is similar to deck member (610) described above except as otherwise described below. In this regard, deck member (710) includes a deck surface (712) extending radially between a generally circular radially inner edge (714) and a generally circular radially outer edge (716). Deck member (710) has a central opening (718) defined by radially inner edge (714) and having an inner diameter that is just slightly larger than the outer diameter defined by knife member (340). Deck member (710) is thus configured to permit knife member (340) to translate longitudinally through the central opening concurrently with longitudinal translation of staple driver member (350). In particular, knife member (340) is configured to actuate relative to deck member (710) between a proximal retracted position and a distal extended position, where cutting edge (342) is proximal to deck surface (712) in the proximal retracted position and distal to deck surface (712) in the distal extended position.

Deck surface (712) of the present version has a single annular array of circumferentially-alternating non-tangential and tangential X-shaped staple openings (620, 720) arranged to align with corresponding arrays of X-shaped staple drivers (not shown) such as X-shaped staple driver assemblies (830) described below, and with corresponding arrays of staple forming pockets (not shown) similar to staple forming pockets (414) of anvil (400) described above. Each staple opening (720) is configured to slidably receive and provide a pathway for a corresponding staple driver to drive a corresponding staple assembly (640) distally through deck member (710) and into a corresponding staple forming pocket when a stapling head assembly (not shown) similar to stapling head assembly (300) is actuated. In the example shown, each staple opening (720) includes overlapping first and second linear staple opening portions (722, 724) which are oriented perpendicularly to each other, and which intersect each other at or near their respective midpoints to define a crossing point of the respective staple opening (720).

In the present version, staple openings (620, 720) are arranged with uniform circumferential spacing about a longitudinal axis (L) of central opening (718), with the midpoints of each staple opening portion (622, 624, 722, 724) (and thus the crossing points of each staple opening (620, 720)) positioned at a same radial distance from longitudinal axis (L) such that the midpoints of each staple opening portion (622, 624, 722, 724) (and thus the crossing points of staple openings (620, 720)) collectively define a reference circle (C). As shown, each staple opening portion (622, 624) is oriented non-tangentially relative to circle (C) in the manner described above. Each first staple opening portion (722) is oriented tangentially relative to circle (C), while each second staple opening portion (724) is oriented radially relative to circle (C). In this manner, staple openings (620, 720) may have substantially the same shape as each other, while the orientations of staple openings (620, 720) may alternate relative to each other circumferentially about longitudinal axis (L), which may result in varying the positions at which staples (641a, 641b) of staple assembly (640) are compressed and/or an increased complexity of any potential leak path between staples (641a, 641b). In any event, the X-shaped staple openings (620, 720) may enable the annular array of formed staple assemblies (640) driven from deck member (710) to expand radially while maintaining a secure seal in a manner similar to that described above in connection with FIGS. 16A-16B.

D. Exemplary X-Shaped Staple Driver Assembly

Figure 18:
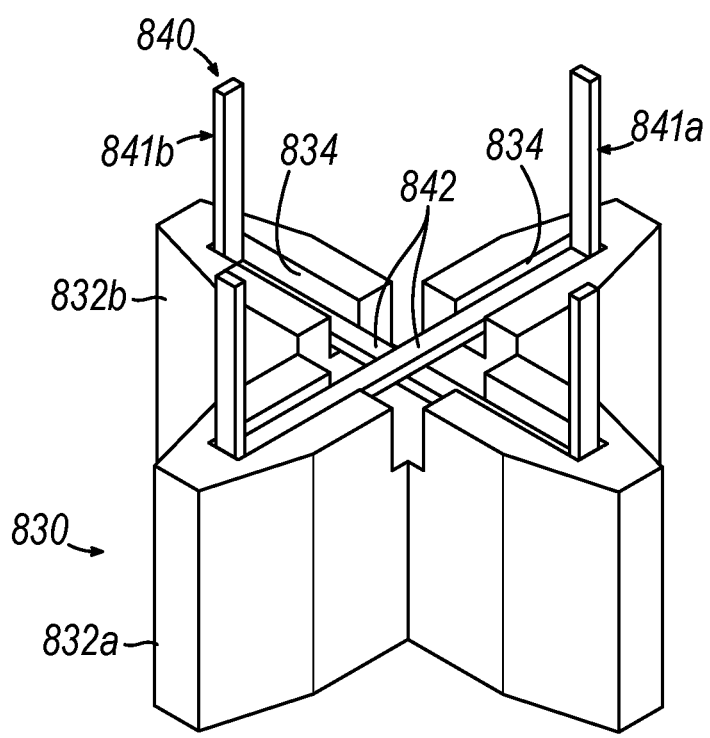
FIG. 18 depicts a top perspective view of an exemplary X-shaped staple driver and another exemplary X-shaped staple assembly for use with the deck members of FIGS. 10 and 17.

FIG. 18 depicts an exemplary X-shaped staple driver assembly (830) for use with deck member (610) and/or deck member (710) described above. Staple driver assembly (830) is similar to staple drivers (352) described above except as otherwise described below. In this regard, staple driver assemblies (830) may be arranged to correspond with the arrangement of X-shaped staple openings (620, 720) of deck member (610) and/or deck member (710), and with staple forming pockets (not shown) of an anvil (not shown), similar to staple forming pockets (414) of anvil (400) described above. Staple driver assembly (830) may further be configured to drive a corresponding X-shaped staple assembly (640, 840) distally into a corresponding staple forming pocket when a stapling head assembly (not shown) such as stapling head assembly (300) is actuated.

Staple driver assembly (830) of the present version includes integrated first and second staple drivers (832a, 832b) which are oriented perpendicularly to each other, and which intersect each other at or near their respective midpoints for driving respective staples (841a, 841b) of staple assembly (840). In this regard, each staple driver (832a, 832b) includes at least one longitudinal groove (834) configured to cradle the crown (842) of the corresponding staple (841a, 841b) of staple assembly (840).

It will be appreciated that staple drivers (832a, 832b) may be unitarily secured to each other. It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

E. Exemplary Deck Member with Two Arrays of X-Shaped Staple Openings

Figure 19:
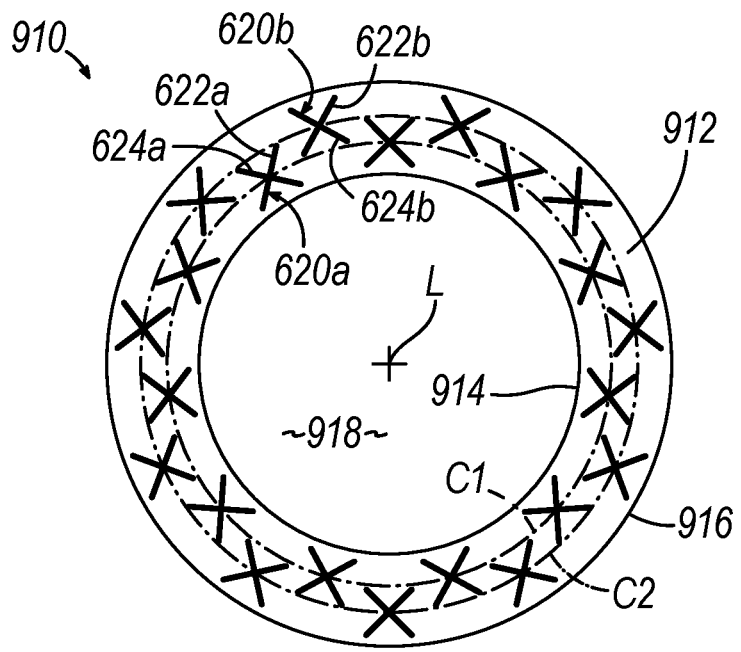
FIG. 19 depicts a top plan view of another exemplary deck member for use with the circular stapler of FIG. 1 and having two concentric annular arrays of X-shaped staple openings.

FIG. 19 depicts an exemplary deck member (910) for use with instrument (10) described above. Deck member (910) is similar to deck member (610) described above except as otherwise described below. In this regard, deck member (910) includes a deck surface (912) extending radially between a generally circular radially inner edge (914) and a generally circular radially outer edge (916). Deck member (910) has a central opening (918) defined by radially inner edge (914) and having an inner diameter that is just slightly larger than the outer diameter defined by knife member (340). Deck member (910) is thus configured to permit knife member (340) to translate longitudinally through the central opening concurrently with longitudinal translation of staple driver member (350). In particular, knife member (340) is configured to actuate relative to deck member (910) between a proximal retracted position and a distal extended position, where cutting edge (342) is proximal to deck surface (912) in the proximal retracted position and distal to deck surface (912) in the distal extended position.

Deck surface (912) of the present version has two concentric annular arrays of X-shaped staple openings (620a, 620b) arranged to align with corresponding arrays of X-shaped staple drivers (not shown) such as X-shaped staple driver assemblies (830) described above, and with corresponding arrays of staple forming pockets (not shown) similar to staple forming pockets (414) of anvil (400) described above. In the example shown, each staple opening (620a, 620b) includes overlapping first and second linear staple opening portions (622a, 622b, 624a, 624b) which are oriented perpendicularly to each other, and which intersect each other at or near their respective midpoints to define a crossing point of the respective staple opening (620a, 620b).

In the present version, staple openings (620a, 620b) are arranged in a radially inner annular array of staple openings (620a) and a radially outer annular array of staple openings (620b). More particularly, radially inner staple openings (620a) are arranged with uniform circumferential spacing about a longitudinal axis (L) of central opening (918), with the midpoints of each staple opening portion (622a, 624a) (and thus the crossing points of each radially inner staple opening (620a)) positioned at a first radial distance from longitudinal axis (L) such that the midpoints of each staple opening portion (622a, 624a) collectively define a first reference circle (C1). Likewise, radially outer staple openings (620b) are arranged with uniform circumferential spacing about longitudinal axis (L) of central opening (918), with the midpoints of each staple opening portion (622b, 624b) (and thus the crossing points of each radially outer staple opening (620b)) positioned at a second radial distance from longitudinal axis (L) greater than the first radial distance such that the midpoints of each staple opening portion (622b, 624b) collectively define a second reference circle (C2) that is radially outward relative to first reference circle (C1). As shown, each staple opening portion (622a, 622b, 624a, 624b) is oriented non-tangentially relative to circle (C) in a manner similar to that described above in connection with FIGS. 10-12. In the example shown, each radially outer staple opening (620b) is positioned circumferentially between a corresponding pair of radially inner staple openings (620a). In any event, the X-shaped staple openings (620a, 620b) may enable the annular arrays of formed staple assemblies (640) driven from deck member (910) to expand radially while maintaining a secure seal in a manner similar to that described above in connection with FIGS. 16A-16B.

F. Exemplary Deck Member with Alternating Linear and X-Shaped Staple Openings

Figure 20:
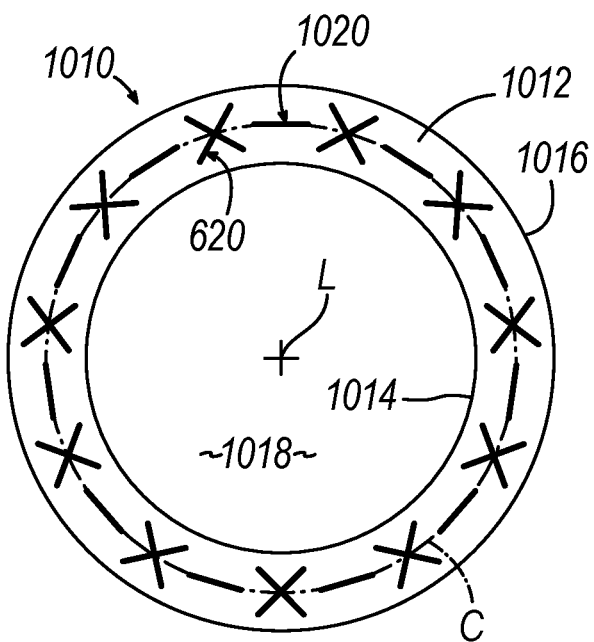
FIG. 20 depicts a top plan view of another exemplary deck member for use with the circular stapler of FIG. 1 and having a single annular array of alternating linear and X-shaped staple openings.

FIG. 20 depicts an exemplary deck member (1010) for use with instrument (10) described above. Deck member (1010) is similar to deck member (610) described above except as otherwise described below. In this regard, deck member (1010) includes a deck surface (1012) extending radially between a generally circular radially inner edge (1014) and a generally circular radially outer edge (1016). Deck member (1010) has a central opening (1018) defined by radially inner edge (1014) and having an inner diameter that is just slightly larger than the outer diameter defined by knife member (340). Deck member (1010) is thus configured to permit knife member (340) to translate longitudinally through the central opening concurrently with longitudinal translation of staple driver member (350). In particular, knife member (340) is configured to actuate relative to deck member (1010) between a proximal retracted position and a distal extended position, where cutting edge (342) is proximal to deck surface (1012) in the proximal retracted position and distal to deck surface (1012) in the distal extended position.

Deck surface (1012) of the present version has a single annular array of circumferentially-alternating X-shaped and linear staple openings (620, 1020) arranged to align with corresponding arrays of circumferentially-alternating X-shaped and linear staple drivers (not shown) such as X-shaped staple driver assemblies (830) and linear staple driver assemblies (352) described above, and with corresponding arrays of staple forming pockets (not shown) similar to staple forming pockets (414) of anvil (400) described above. Each staple opening (1020) is configured to slidably receive and provide a pathway for a corresponding staple driver to drive a corresponding staple assembly (640) distally through deck member (1010) and into a corresponding staple forming pocket when a stapling head assembly (not shown) similar to stapling head assembly (300) is actuated.

In the present version, staple openings (620, 1020) are arranged with uniform circumferential spacing about a longitudinal axis (L) of central opening (1018), with the midpoints of each staple opening portion (622, 624) (and thus the crossing points of each staple opening (620)) and of each staple opening (1020) positioned at a same radial distance from longitudinal axis (L) such that the midpoints of each staple opening portion (622, 624) (and thus the crossing points of each staple opening (620)) and of each staple opening (1020) collectively define a reference circle (C). As shown, each staple opening portion (622, 624) is oriented non-tangentially relative to circle (C) in the manner described above. Each staple opening (1020) is oriented tangentially relative to circle (C). In any event, the X-shaped staple openings (620) may enable the annular array of formed staple assemblies (640) driven from deck member (1010) to expand radially while maintaining a secure seal in a manner similar to that described above in connection with FIGS. 16A-16B.

Figure 21:
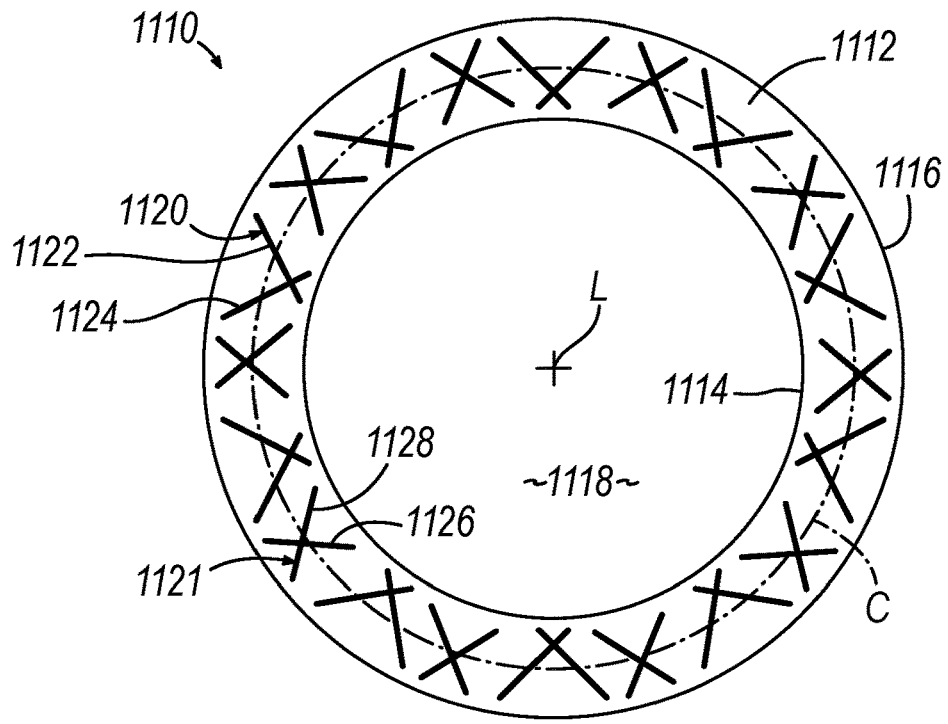
FIG. 21 depicts a top plan view of another exemplary deck member for use with the circular stapler of FIG. 1 and having a single annular array of alternating deep and shallow X-shaped staple openings.

G. Exemplary Deck Member with Alternating Deep and Shallow X-Shaped Staple Openings FIG. 21 depicts an exemplary deck member (1110) for use with instrument (10) described above. Deck member (1110) is similar to deck member (610) described above except as otherwise described below. In this regard, deck member (1110) includes a deck surface (1112) extending radially between a generally circular radially inner edge (1114) and a generally circular radially outer edge (1116). Deck member (1110) has a central opening (1118) defined by radially inner edge (1114) and having an inner diameter that is just slightly larger than the outer diameter defined by knife member (340). Deck member (1110) is thus configured to permit knife member (340) to translate longitudinally through the central opening concurrently with longitudinal translation of staple driver member (350). In particular, knife member (340) is configured to actuate relative to deck member (1110) between a proximal retracted position and a distal extended position, where cutting edge (342) is proximal to deck surface (1112) in the proximal retracted position and distal to deck surface (1112) in the distal extended position.

Deck surface (1112) of the present version has a single annular array of circumferentially-alternating deep X-shaped and shallow X-shaped staple openings (1120, 1121) arranged to align with a corresponding array of circumferentially-alternating deep X-shaped and shallow X-shaped staple drivers (not shown) similar to X-shaped staple driver assemblies (830) described above, and with a corresponding array of circumferentially-alternating deep X-shaped and shallow X-shaped staple forming pockets (not shown) similar to staple forming pockets (414) of anvil (400) described above. Each staple opening (1120, 1121) is configured to slidably receive and provide a pathway for a corresponding staple driver to drive a corresponding staple assembly (not shown) similar to staple assembly (640) distally through deck member (1110) and into a corresponding staple forming pocket when a stapling head assembly (not shown) similar to stapling head assembly (300) is actuated. In the example shown, each staple opening (1120) includes overlapping first and second linear staple opening portions (1122, 1124) which are oriented obliquely to each other, and which intersect each other radially inwardly of their respective midpoints to define a crossing point of the respective staple opening (1120). Each staple opening (1121) includes overlapping first and second linear staple opening portions (1126, 1128) which are oriented obliquely to each other, and which intersect each other radially outwardly of their respective midpoints to define a crossing point of the respective staple opening (1121).

In the present version, staple openings (1120, 1121) are arranged with uniform circumferential spacing about a longitudinal axis (L) of central opening (1118), with the midpoints of each staple opening portion (1122, 1124, 1126, 1128) positioned at a same radial distance from longitudinal axis (L) such that the midpoints of each staple opening portion (1122, 1124, 1126, 1128) collectively define a reference circle (C). As shown, each staple opening portion (1122, 1124, 1126, 1128) is oriented non-tangentially relative to circle (C) in a manner similar to that described above in connection with FIGS. 10-12. In some versions, at least a portion of each deep X-shaped staple opening (1120) (e.g., a radially outer portion of its first staple opening portion (1122)) may be aligned in a radial direction with at least a portion of a corresponding clockwise-adjacent shallow X-shaped staple opening (1121) (e.g., a radially inner portion of its first staple opening portion (1126). In addition, or alternatively, at least a portion of each shallow X-shaped staple opening (1121) (e.g., a radially inner portion of its second staple opening portion (1128)) may be aligned in a radial direction with at least a portion of a corresponding clockwise-adjacent deep X-shaped staple opening (1120) (e.g., a radially outer portion of its second staple opening portion (1124)). It will be appreciated that such radial alignment(s) may increase the complexity of any potential leak path between staples of formed staple assemblies driven from deck member (1110). In any event, the X-shaped staple openings (1120, 1121) may enable the annular array of formed staple assemblies driven from deck member (1110) to expand radially while maintaining a secure seal in a manner similar to that described above in connection with FIGS. 16A-16B.

H. Exemplary Deck Member with Overlapping Deep X-Shaped Staple Openings

Figure 22:
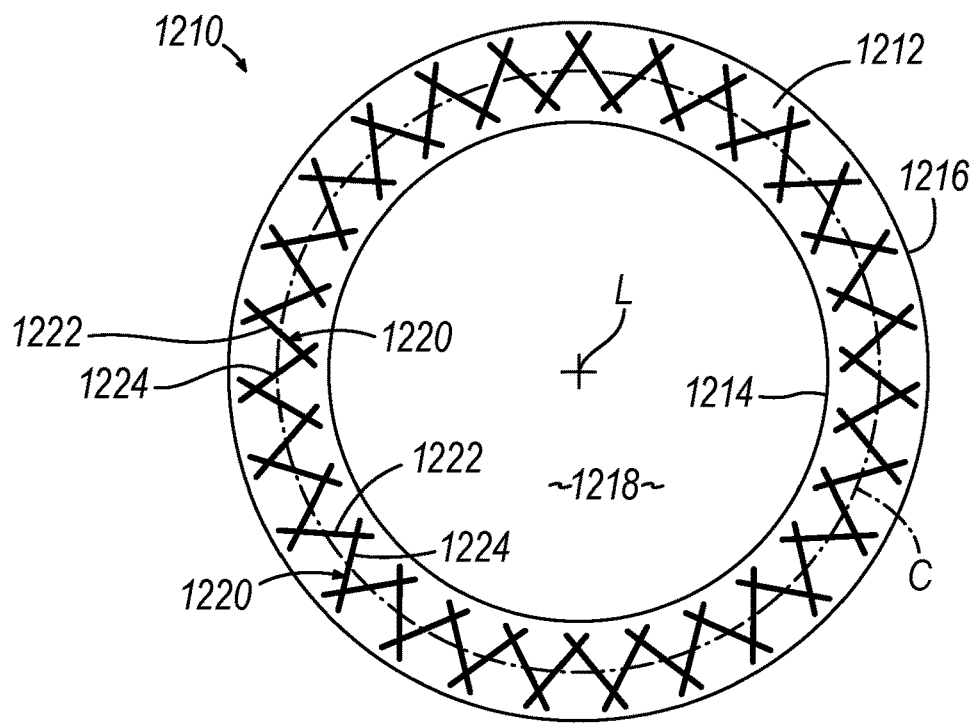
FIG. 22 depicts a top plan view of another exemplary deck member for use with the circular stapler of FIG. 1 and having a single annular array of overlapping deep X-shaped staple openings.

FIG. 22 depicts an exemplary deck member (1210) for use with instrument (10) described above. Deck member (1210) is similar to deck member (610) described above except as otherwise described below. In this regard, deck member (1210) includes a deck surface (1212) extending radially between a generally circular radially inner edge (1214) and a generally circular radially outer edge (1216). Deck member (1210) has a central opening (1218) defined by radially inner edge (1214) and having an inner diameter that is just slightly larger than the outer diameter defined by knife member (340). Deck member (1210) is thus configured to permit knife member (340) to translate longitudinally through the central opening concurrently with longitudinal translation of staple driver member (350). In particular, knife member (340) is configured to actuate relative to deck member (1210) between a proximal retracted position and a distal extended position, where cutting edge (342) is proximal to deck surface (1212) in the proximal retracted position and distal to deck surface (1212) in the distal extended position.

Deck surface (1212) of the present version has a single annular array of deep X-shaped staple openings (1220) arranged to align with a corresponding array of deep X-shaped staple drivers (not shown) similar to X-shaped staple driver assemblies (830) described above, and with a corresponding array of deep X-shaped staple forming pockets (not shown) similar to staple forming pockets (414) of anvil (400) described above. Each staple opening (1220) is configured to slidably receive and provide a pathway for a corresponding staple driver to drive a corresponding staple assembly (not shown) similar to staple assembly (640) distally through deck member (1210) and into a corresponding staple forming pocket when a stapling head assembly (not shown) similar to stapling head assembly (300) is actuated. In the example shown, each staple opening (1220) includes overlapping first and second linear staple opening portions (1222, 1224) which are oriented obliquely to each other, and which intersect each other radially inwardly of their respective midpoints to define a crossing point of the respective staple opening (1220).

In the present version, staple openings (1220) are arranged with uniform circumferential spacing about a longitudinal axis (L) of central opening (1218), with the midpoints of each staple opening portion (1222, 1224) positioned at a same radial distance from longitudinal axis (L) such that the midpoints of each staple opening portion (1222, 1224) collectively define a reference circle (C). As shown, each staple opening portion (1222, 1224) is oriented non-tangentially relative to circle (C) in a manner similar to that described above in connection with FIGS. 10-12. In some versions, at least a portion of each staple opening (1220) (e.g., a radially outer portion of its first staple opening portion (1222)) may intersect at least a portion of the clockwise-adjacent staple opening (1120) (e.g., a radially outer portion of its second staple opening portion (1222). It will be appreciated that such intersecting may increase the complexity of any potential leak path between staples of formed staple assemblies driven from deck member (1210). In any event, the X-shaped staple openings (1220) may enable the annular array of formed staple assemblies driven from deck member (1210) to expand radially while maintaining a secure seal in a manner similar to that described above in connection with FIGS. 16A-16B.

Exemplary Deck Member with Staple Openings in Undulating Pattern

Figure 23:
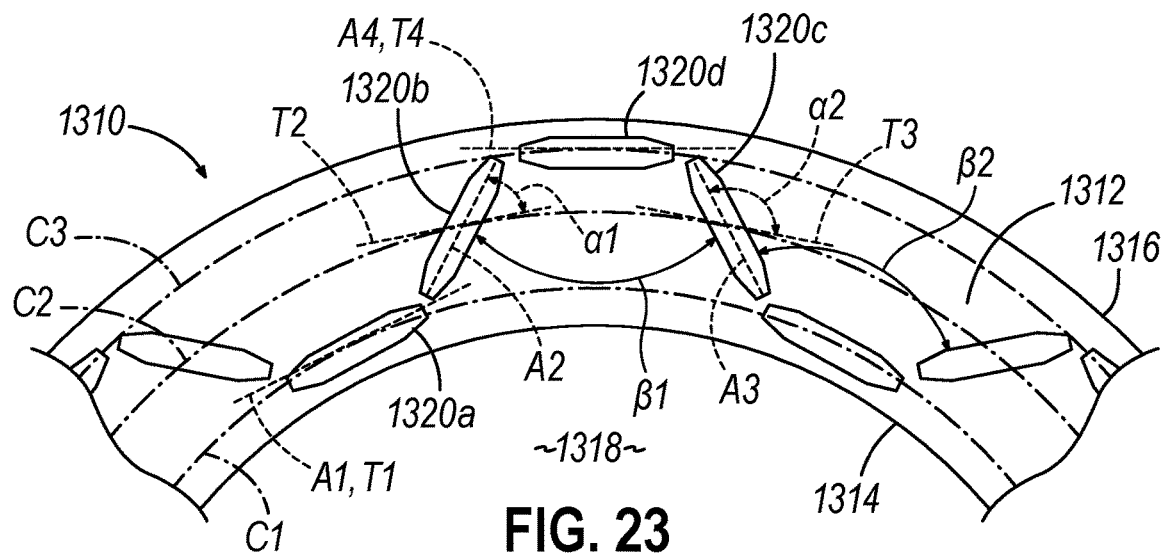
FIG. 23 depicts a partial top plan view of another exemplary deck member for use with the circular stapler of FIG. 1 and having three concentric annular arrays of staple openings.

FIG. 23 depicts an exemplary deck member (1310) for use with instrument (10) described above. Deck member (1310) is similar to deck member (510) described above except as otherwise described below. In this regard, deck member (1310) includes a deck surface (1312) extending radially between a generally circular radially inner edge (1314) and a generally circular radially outer edge (1316). Deck member (1310) has a central opening (1318) defined by radially inner edge (1314) and having an inner diameter that is just slightly larger than the outer diameter defined by knife member (340). Deck member (1310) is thus configured to permit knife member (340) to translate longitudinally through the central opening concurrently with longitudinal translation of staple driver member (350). In particular, knife member (340) is configured to actuate relative to deck member (1310) between a proximal retracted position and a distal extended position, where cutting edge (342) is proximal to deck surface (1312) in the proximal retracted position and distal to deck surface (1312) in the distal extended position.

Deck surface (1312) of the present version has three concentric annular arrays of linear staple openings (1320a, 1320b, 1320c, 1320d) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (1320a, 1320b, 1320c, 1320d) is configured to slidably receive and provide a pathway for a corresponding staple driver to drive a corresponding staple (90a, 90b, 90c, 90d) (FIGS. 24A-24B) distally through deck member (1310) and into a corresponding staple forming pocket when a stapling head assembly (not shown) similar to stapling head assembly (300) is actuated.

In the present version, staple openings (1320a, 1320b, 1320c, 1320d) are arranged in a radially inner annular array of first staple openings (1320a), a radially intermediate annular array of circumferentially-alternating second and third staple openings (1320b, 1320c), and a radially outer annular array of fourth staple openings (1320d). More particularly, radially inner staple openings (1320a) are arranged with uniform circumferential spacing about a longitudinal axis (not shown) of central opening (1318), with the midpoints of each radially inner staple opening (1320a) positioned at a first radial distance from the longitudinal axis such that the midpoints of radially inner staple openings (1320a) collectively define a first reference circle (C1). As shown, each radially inner staple opening (1320a) is oriented tangentially relative to first circle (C1). In this regard, first staple openings (1320a) each extend along a respective first axis (A1) colinear with a corresponding reference line (T1) that extends tangentially to first circle (C1) through the respective midpoint.

Likewise, radially intermediate staple openings (1320b, 1320c) are arranged with uniform circumferential spacing about the longitudinal axis of central opening (1318), with the midpoints of each radially intermediate staple openings (1320b, 1320c) positioned at a second radial distance from the longitudinal axis greater than the first radial distance, such that the midpoints of radially intermediate staple openings (1320b, 1320c) collectively define a second reference circle (C2) that is radially outward relative to the first reference circle (C1). As shown, each radially intermediate staple opening (1320b, 1320c) is oriented non-tangentially relative to second circle (C2). In this regard, second staple openings (1320b) each extend along a respective second axis (A2) oriented at a first oblique angle ($\alpha1$) relative to a corresponding reference line (T2) that extends tangentially to second circle (C2) through the respective midpoint, and third staple openings (1320c) each extend along a respective third axis (A3) oriented at a second oblique angle ($\alpha2$) relative to a corresponding reference line (T3) that extends tangentially to second circle (C2) through the respective midpoint. In the example shown, first angle ($\alpha1$) is acute such that each second staple opening (1320b) extends generally radially outwardly in a clockwise direction, while second angle (α2) is obtuse such that each third staple opening (1320c) extends generally radially inwardly in a clockwise direction. In some versions, first and second angles (α1, α2) may be supplementary to each other. For example, first angle (α1) may be approximately 30° and second angle (α2) may be approximately 150°. In any event, each second staple opening (1320b) and a corresponding clockwise-adjacent third staple opening (1320c) may collectively define a first internal angle (β1) which opens toward inner edge (1314), while each third staple opening (1320c) and a corresponding clockwise-adjacent second staple opening (1320b) may collectively define a second internal angle (β2) which opens toward outer edge (1316).

Likewise, radially outer staple openings (1320d) are arranged with uniform circumferential spacing about the longitudinal axis of central opening (1318), with the midpoints of each radially outer staple opening (1320d) positioned at a third radial distance from the longitudinal axis greater than the second radial distance, such that the midpoints of radially outer staple openings (1320d) collectively define a third reference circle (C3) that is radially outward relative to the second reference circle (C2). As shown, each radially outer staple opening (1320d) is oriented tangentially relative to third circle (C3). In this regard, fourth staple openings (1320d) each extend along a respective fourth axis (A4) colinear with a corresponding reference line (T4) that extends tangentially to third circle (C3) through the respective midpoint.

In the example shown, radially inner staple openings (1320a) are each generally centered between a corresponding circumferentially-adjacent pair of radially outer staple openings (1320d) in the circumferential direction, and radially outer staple openings (1320d) are each generally centered between a corresponding circumferentially-adjacent pair of radially inner staple openings (1320a). Radially intermediate staple openings (1320b, 1320c) each extend radially and circumferentially between respective ends of corresponding circumferentially-adjacent radially inner and radially outer staple openings (1320a, 1320d). More particularly, second staple openings (1320b) each generally extend radially outwardly in the clockwise direction from a radially inner end near a clockwise end of the corresponding radially inner staple opening (1320a) toward a radially outer end near a counterclockwise end of the corresponding radially outer staple opening (1320d). Third staple openings (1320c) each generally extend radially inwardly in the clockwise direction from a radially outer end near a clockwise end of the corresponding radially outer staple opening (1320d) toward a radially inner end near a counterclockwise end of the corresponding radially inner staple opening (1320a).

Due to the relative positions and orientations of staple openings (1320a, 1320b, 1320c, 1320d), the annular arrays of staple openings (1320a, 1320b, 1320c, 1320d) may collectively define an undulating curvilinear staple opening pattern. In this regard, each first staple opening (1320a), corresponding clockwise-adjacent second staple opening (1320b), and corresponding counterclockwise-adjacent third staple opening (1320c) may collectively define a respective U-shaped staple opening pattern which faces radially outwardly (e.g., opens toward outer edge (1316)), while each fourth staple opening (1320d), corresponding counterclockwise-adjacent second staple opening (1320b), and corresponding clockwise-adjacent third staple opening (1320c) may collectively define a respective U-shaped staple opening pattern which faces radially inwardly (e.g., opens toward inner edge (1314)). The undulating staple opening pattern may enable the annular arrays of formed staples (90a, 90b, 90c, 90d) driven from deck member (1310) to expand radially while maintaining a secure seal as described in greater detail below.

Figure 24A:
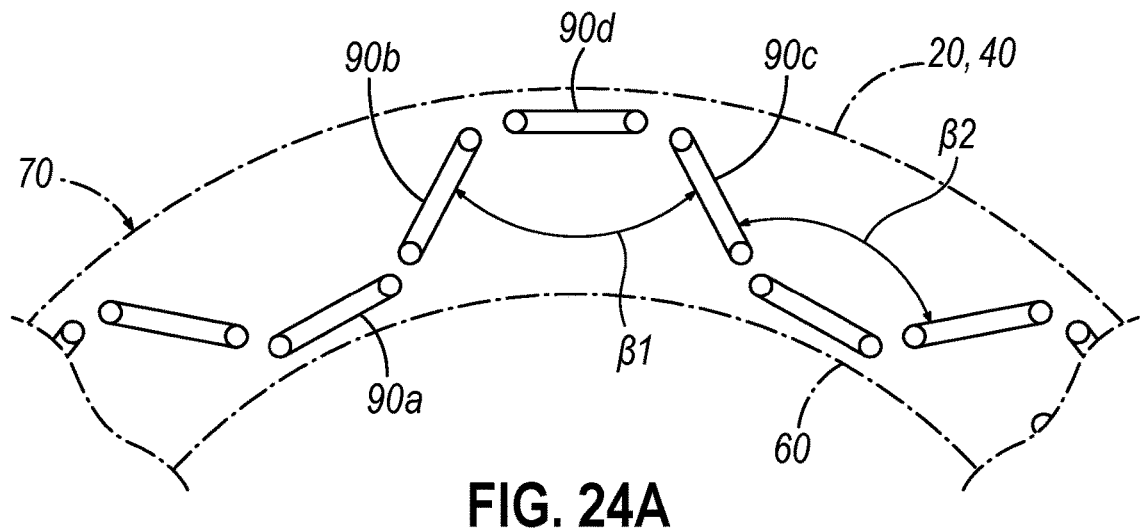
FIG. 24A depicts a partial top plan view of three concentric annular arrays of staples driven from the deck member of FIG. 23, showing the annular arrays of staples in a radially unexpanded state.
Figure 24B:
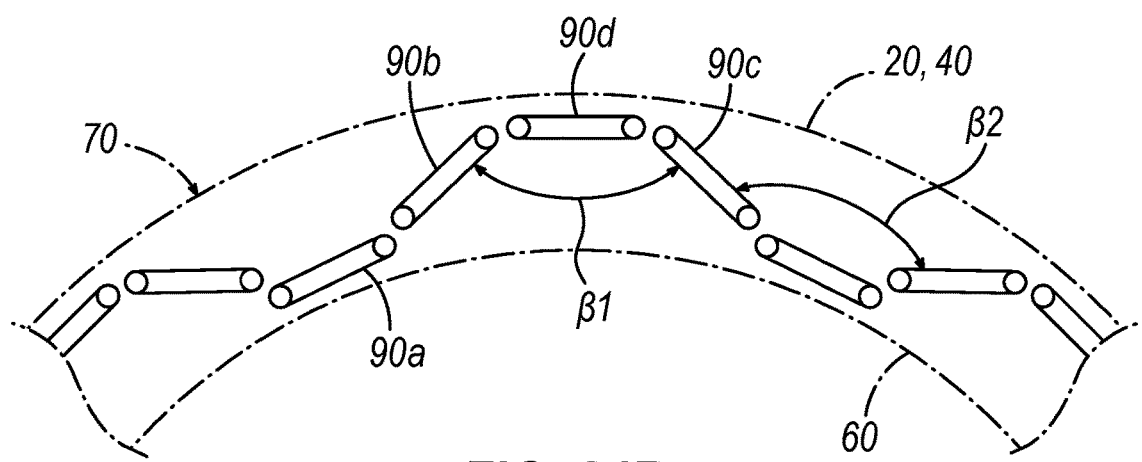
FIG. 24B depicts a partial top plan view of the annular arrays of staples of FIG. 24A, showing the annular arrays of staples in a radially expanded state.

Referring now to FIGS. 24A-24B, the annular arrays of formed staples (90a, 90b, 90c, 90d) driven from deck member (1310) to secure tubular anatomical structures (20, 40) at anastomosis (70) may define an undulating curvilinear staple pattern corresponding to the undulating staple opening pattern defined by the annular arrays of staple openings (1320a, 1320b, 1320c, 1320d). In this regard, formed staples (90a, 90b, 90c, 90d) may initially be positioned and oriented in manners corresponding to the respective staple openings (1320a, 1320b, 1320c, 1320d) so as to define the same internal angles ((31, (32, (33, (34) while anastomosis (70) is maintained in an unexpanded state, as shown in FIG. 24A. Formed staples (90a, 90b, 90c, 90d) may each be reoriented to accommodate expansion of at least a portion of anastomosis (70) (e.g., the inner diameter of the anastomosis (70) defined by the severed edge (60)) to one or more expanded states without stretching the puncture openings in tubular anatomical structures (20, 40) through which formed staples (90a, 90b, 90c, 90d) extend, as shown in FIG. 24B. For example, the radially intermediate formed staples (90b, 90c) may each be generally pivoted about their respective radially inner and/or outer ends such that their respective radially inner ends are rotated away from each other and their respective radially outer ends are rotated toward each other, thereby increasing the first internal angle (β1) and decreasing the second internal angle (β2), to accommodate expansion of anastomosis (70) in a first radial direction to a first expanded state (FIG. 24B). Similarly, the radially intermediate formed staples (90b, 90c) may each be generally pivoted about their respective radially inner and/or outer ends such that their respective radially inner ends are rotated toward each other and their respective radially outer ends are rotated away from each other, thereby decreasing the first internal angle (β1) and increasing the second internal angle (β2), to accommodate expansion of anastomosis (70) in a second radial direction to a second expanded state (not shown).

Figure 25:
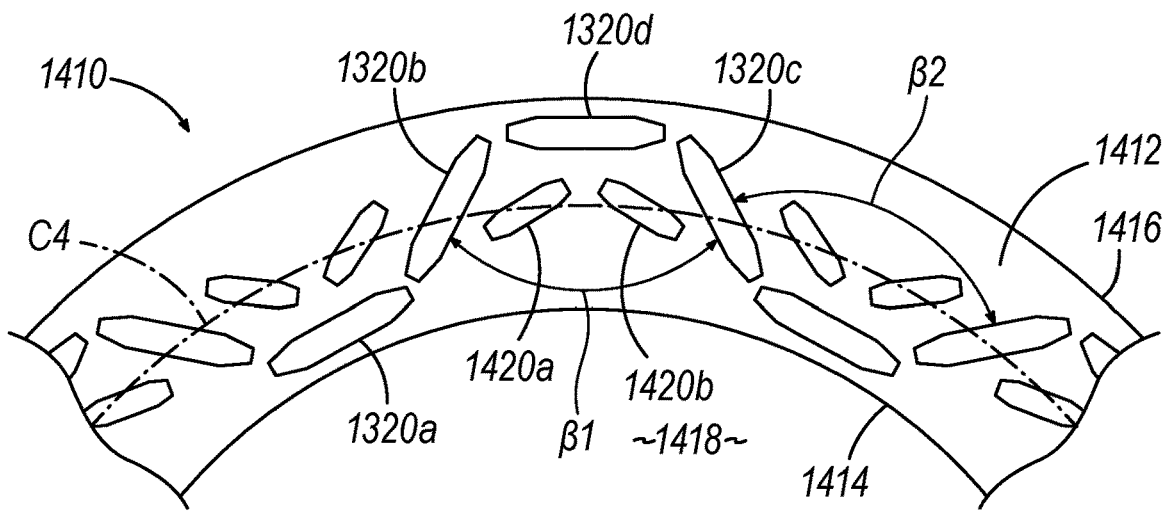
FIG. 25 depicts a partial top plan view of another exemplary deck member for use with the circular stapler of FIG. 1 and having four concentric annular arrays of staples.

J. Exemplary Deck Member with Large Staple Openings in Undulating Pattern and with Nested Small Staple Openings FIG. 25 depicts an exemplary deck member (1410) for use with instrument (10) described above. Deck member (1410) is similar to deck member (1310) described above except as otherwise described below. In this regard, deck member (1410) includes a deck surface (1412) extending radially between a generally circular radially inner edge (1414) and a generally circular radially outer edge (1416). Deck member (1410) has a central opening (1418) defined by radially inner edge (1414) and having an inner diameter that is just slightly larger than the outer diameter defined by knife member (340). Deck member (1410) is thus configured to permit knife member (340) to translate longitudinally through the central opening concurrently with longitudinal translation of staple driver member (350). In particular, knife member (340) is configured to actuate relative to deck member (1410) between a proximal retracted position and a distal extended position, where cutting edge (342) is proximal to deck surface (1412) in the proximal retracted position and distal to deck surface (1412) in the distal extended position.

Deck surface (1412) of the present version has four concentric annular arrays of linear staple openings (1320a, 1320b, 1320c, 1320d, 1420a, 1420b, 1420c, 1420d)

arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (1320*a*, 1320*b*, 1320*c*, 1320*d*, 1420*a*, 1420*b*, 1420*c*, 1420*d*) is configured to slidably receive and provide a pathway for a corresponding staple driver to drive a corresponding staple (90*a*, 90*b*, 90*c*, 90*d*) (FIGS. 24A-24B) distally through deck member (1410) and into a corresponding staple forming pocket when a stapling head assembly (not shown) similar to stapling head assembly (300) is actuated. In the example shown, staple openings (1320*a*, 1320*b*, 1320*c*, 1320*d*, 1420*a*, 1420*b*, 1420*c*, 1420*d*) include relatively large staple openings (1320*a*, 1320*b*, 1320*c*, 1320*d*) and relatively small staple openings (also referred to herein as auxiliary staple openings) (1420*a*, 1420*b*, 1420*c*, 1420*d*).

In the present version, the relatively large staple openings (1320*a*, 1320*b*, 1320*c*, 1320*d*) are arranged to define an undulating curvilinear staple opening pattern as described above. The relatively small staple openings (1420*a*, 1420*b*, 1420*c*, 1420*d*) are arranged circumferentially about the longitudinal axis (L) of central opening (1418), with the midpoints of each small staple opening (1420*a*, 1420*b*, 1420*c*, 1420*d*) positioned at a fourth radial distance from longitudinal axis (L) between the first and second radial distances such that the midpoints of small staple openings (1420*a*, 1420*b*, 1420*c*, 1420*d*) collectively define a fourth reference circle (C4) radially between the first and second circles (C1, C2). In some versions, fourth circle (C4) may be offset from (e.g., radially inward of) a circumferential midline between inner and outer edges (1414, 1416). As shown, each small staple opening (1420*a*, 1420*b*, 1420*c*, 1420*d*) is oriented non-tangentially relative to fourth circle (C4), with each first and fourth staple opening (1420*a*, 1420*d*) extending generally radially outwardly in a clockwise direction and with each second and third staple opening (1420*b*, 1420*c*) extending generally radially inwardly in a clockwise direction. Each first staple opening (1420*c*) and a corresponding clockwise-adjacent second staple opening (1420*b*) are captured within the first internal angle (β1) and nested within the U-shaped staple pattern defined by the corresponding large staple openings (1320*b*, 1320*c*, 1320*d*), while each third staple opening (1420*c*) and a corresponding clockwise-adjacent fourth staple opening (1420*d*) are captured within the second internal angle (β2) and nested within the U-shaped staple pattern defined by the corresponding large staple openings (1320*a*, 1320*b*, 1320*c*).

In the example shown, at least a portion of each first small staple opening (1420*a*) (e.g., a radially outer portion thereof) may be aligned in a radial direction with at least a portion of a corresponding radially-adjacent fourth large staple opening (1320*d*) (e.g., a counterclockwise portion thereof), and at least a portion of each first small staple opening (1420*a*) (e.g., a radially inner portion thereof) may be aligned in a radial direction with at least a portion of a corresponding counterclockwise-adjacent second large staple opening (1320*b*) (e.g., a clockwise portion thereof).

In addition, or alternatively, at least a portion of each second small staple opening (1420*b*) (e.g., a radially outer portion thereof) may be aligned in a radial direction with at least a portion of a corresponding radially-adjacent fourth large staple opening (1320*d*) (e.g., a clockwise portion thereof), and at least a portion of each second small staple opening (1420*b*) (e.g., a radially inner portion thereof) may be aligned in a radial direction with at least a portion of a corresponding clockwise-adjacent third large staple opening (1320*c*) (e.g., a counterclockwise portion thereof).

In addition, or alternatively, at least a portion of each third small staple opening (1420*c*) (e.g., a radially inner portion thereof) may be aligned in a radial direction with at least a portion of a corresponding radially-adjacent first large staple opening (1320*a*) (e.g., a counterclockwise portion thereof), and at least a portion of each third small staple opening (1420*c*) (e.g., a radially outer portion thereof) may be aligned in a radial direction with at least a portion of a corresponding counterclockwise-adjacent third large staple opening (1320*c*) (e.g., a clockwise portion thereof).

In addition, or alternatively, at least a portion of each fourth small staple opening (1420*d*) (e.g., a radially inner portion thereof) may be aligned in a radial direction with at least a portion of a corresponding radially-adjacent first large staple opening (1320*a*) (e.g., a clockwise portion thereof), and at least a portion of each fourth small staple opening (1420*d*) (e.g., a radially outer portion thereof) may be aligned in a radial direction with at least a portion of a corresponding counterclockwise-adjacent second large staple opening (1320*b*) (e.g., a counterclockwise portion thereof).

It will be appreciated that such radial alignment(s) may increase the complexity of any potential leak path between formed staples (90*a*, 90*b*, 90*c*, 90*d*) driven from deck member (1410). In any event, the undulating staple opening pattern may enable the annular array of formed staples (90*a*, 90*b*, 90*c*, 90*d*) driven from deck member (1410) to expand radially while maintaining a secure seal in a manner similar to that described above in connection with FIGS. 24A-24B.

K. Exemplary Deck Member with Staple Openings in Nested Undulating Patterns

Figure 26:
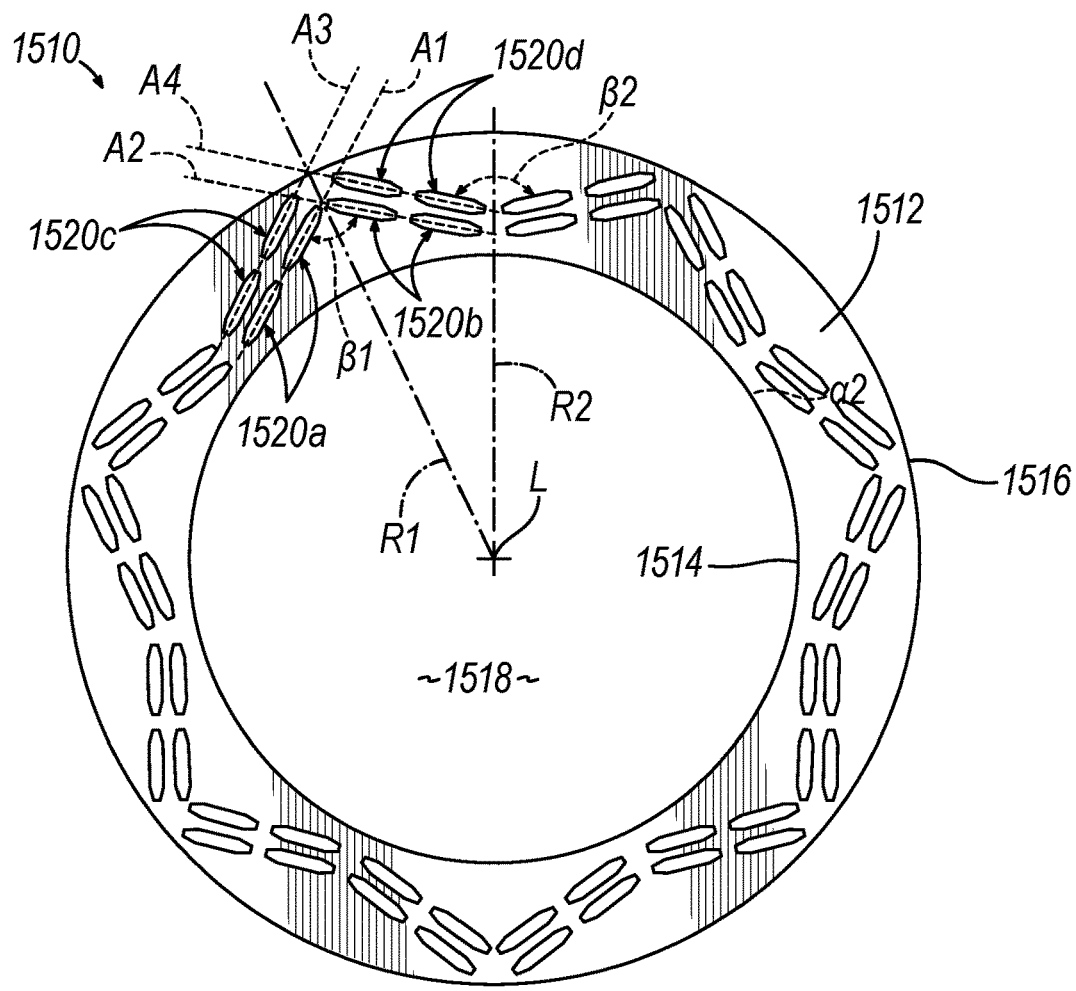
FIG. 26 depicts a top plan view of another exemplary deck member for use with the circular stapler of FIG. 1 and having two concentric star-shaped arrays of linear staple openings.

FIG. 26 depicts an exemplary deck member (1510) for use with instrument (10) described above. Deck member (1510) is similar to deck member (510) described above except as otherwise described below. In this regard, deck member (1510) includes a deck surface (1512) extending radially between a generally circular radially inner edge (1514) and a generally circular radially outer edge (1516). Deck member (1510) has a central opening (1518) defined by radially inner edge (1514) and having an inner diameter that is just slightly larger than the outer diameter defined by knife member (340). Deck member (1510) is thus configured to permit knife member (340) to translate longitudinally through the central opening concurrently with longitudinal translation of staple driver member (350). In particular, knife member (340) is configured to actuate relative to deck member (1510) between a proximal retracted position and a distal extended position, where cutting edge (342) is proximal to deck surface (1512) in the proximal retracted position and distal to deck surface (1512) in the distal extended position.

Deck surface (1512) of the present version has two concentric star-shaped arrays of linear staple openings (1520*a*, 1520*b*, 1520*c*, 1520*d*) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (1520*a*, 1520*b*, 1520*c*, 1520*d*) is configured to slidably receive and provide a pathway for a corresponding staple driver to drive a corresponding staple (90*a*, 90*b*, 90*c*, 90*d*) (FIGS. 27A-27C) distally through deck member (1510) and into a corresponding staple forming pocket when a stapling head assembly (not shown) similar to stapling head assembly (300) is actuated. In some versions, each staple opening (1520a, 1520b, 1520c, 1520d) may have a width of approximately 0.100 inch.

In the present version, staple openings (1520a, 1520b, 1520c, 1520d) are arranged in a radially inner star-shaped array of circumferentially-alternating pairs of inline first and second staple openings (1520a, 1520b) and a radially outer star-shaped array of circumferentially-alternating pairs of inline third and fourth staple openings (1520c, 1520d). More particularly, each pair of first staple openings (1520a) extends radially outwardly in a clockwise direction along a respective first axis (A1), each pair of second staple openings (1520b) extends radially inwardly in a clockwise direction along a respective second axis (A2), each pair of third staple openings (1520c) extends radially outwardly in a clockwise direction along a respective third axis (A3), and each pair of fourth staple openings (1520d) extends radially inwardly in a clockwise direction along a respective fourth axis (A4). Each pair of first staple openings (1520a) and a corresponding clockwise-adjacent pair of second staple openings (1520b) may collectively define a first internal angle (β1) which opens toward inner edge (1514), while each pair of second staple openings (1520b) and a corresponding clockwise-adjacent pair of first staple openings (1520a) may collectively define a second internal angle (β2), which opens toward outer edge (1516). In some versions, the first and third axes (A1, A3) are parallel to each other and the second and fourth axes (A2, A4) are parallel to each other such that each pair of third staple openings (1520c) and a corresponding clockwise-adjacent pair of fourth staple openings (1520d) may also collectively define the first internal angle (β1), while each pair of fourth staple openings (1520d) and a corresponding clockwise-adjacent pair of third staple openings (1520c) may also collectively define the second internal angle (β2). In the example shown, the first and second internal angles (β1, β2) are each bifurcated by a corresponding radial reference line (R1, R2) such that staple openings (1520a, 1520b, 1520c, 1520d) are arranged symmetrically (e.g., mirrored) about each radial line (R1, R2). In some versions, the axes (A1, A2, A3, A4) may each be oriented at an angle of approximately 25° or approximately 155° relative to a corresponding reference line (not shown) that is tangential to inner edge (1514) or outer edge (1516) and perpendicular to the corresponding radial line (R1, R2).

In the example shown, radially inner staple openings (1520a, 1520b) are each generally aligned with a corresponding radially outer staple opening (1520c, 1520d) in a radial direction. More particularly, first staple openings (1520a) are each generally aligned with a corresponding third staple opening (1520c) in a radial direction, and second staple openings (1520b) are each generally aligned with a corresponding fourth staple opening (1520d) in a radial direction. While two concentric star-shaped arrays of linear staple openings (1520a, 1520b, 1520c, 1520d) are shown, it will be appreciated that one or more additional concentric star-shaped staple opening arrays may be included.

Due to the relative positions and orientations of staple openings (1520a, 1520b, 1520c, 1520d), the star-shaped arrays of staple openings (1520a, 1520b, 1520c, 1520d) may define a pair of nested undulating curvilinear staple opening patterns. In this regard, each pair of first staple openings (1520a) and corresponding clockwise-adjacent pair of second staple openings (1520b) may collectively define a respective V-shaped staple opening pattern which faces radially inwardly (e.g., opens toward inner edge (1514)), while each pair of second staple openings (1520b) and corresponding clockwise-adjacent pair of first staple openings (1520a) may collectively define a respective V-shaped staple opening pattern which faces radially outwardly (e.g., opens toward outer edge (1516)). Similarly, each pair of third staple openings (1520c) and corresponding clockwise-adjacent pair of fourth staple openings (1520d) may collectively define a respective V-shaped staple opening pattern which faces radially inwardly (e.g., opens toward inner edge (1514)) and captures the V-shaped staple opening pattern defined by the corresponding pairs of first and second staple openings (1520a, 1520b), while each pair of fourth staple openings (1520d) and corresponding clockwise-adjacent pair of third staple openings (1520c) may collectively define a respective V-shaped staple opening pattern which faces radially outwardly (e.g., opens toward outer edge (1516)) and is captured by the V-shaped staple opening pattern defined by the corresponding pairs of first and second staple openings (1520a, 1520b). The nested undulating staple opening patterns may enable the annular arrays of formed staples (90a, 90b, 90c, 90d) driven from deck member (1510) to expand radially while maintaining a secure seal as described in greater detail below.

Figure 27A:
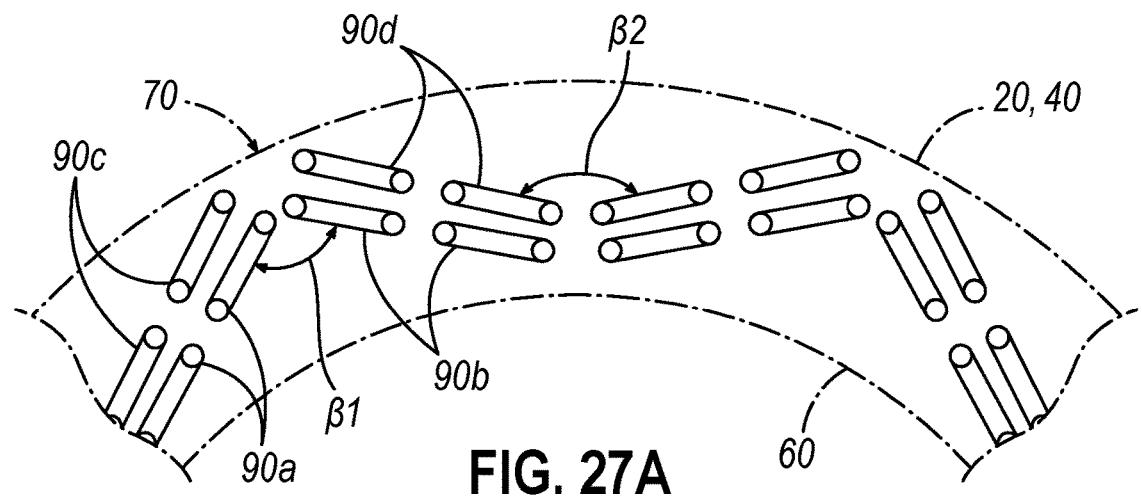
FIG. 27A depicts a partial top plan view of two concentric star-shaped arrays of staples driven from the deck member of FIG. 26, showing the star-shaped arrays of staples in a radially unexpanded state.
Figure 27B:
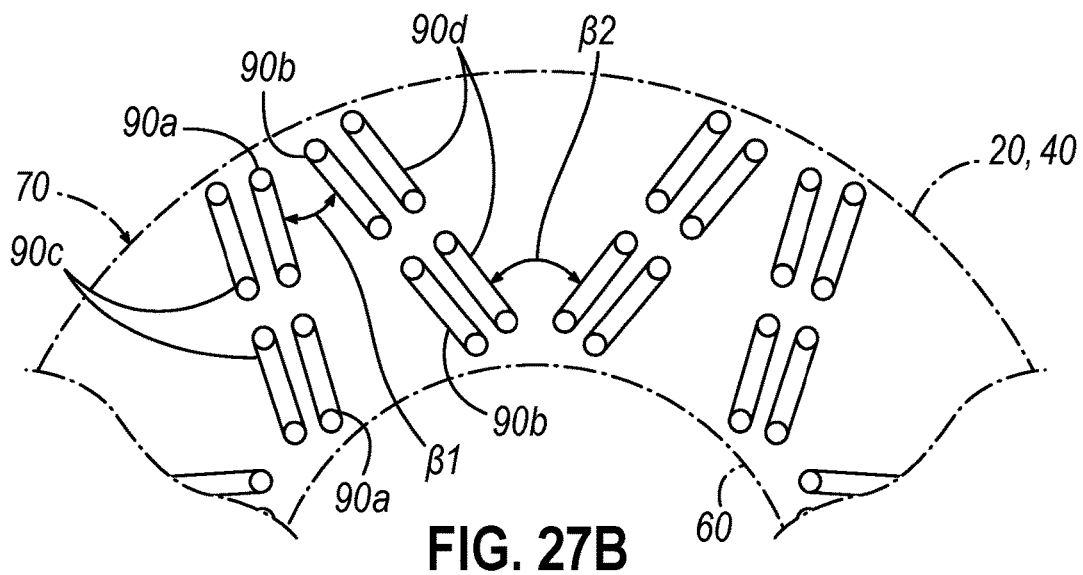
FIG. 27B depicts a partial top plan view of the star-shaped arrays of staples of FIG. 27A, showing the star-shaped arrays of staples in a first radially expanded state.
Figure 27C:
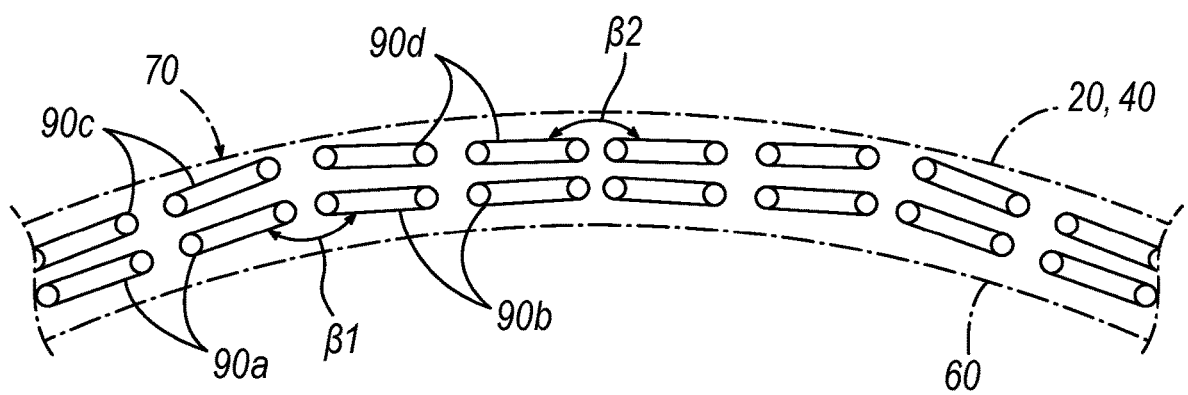
FIG. 27C depicts a partial top plan view of the star-shaped arrays of staples of FIG. 27A, showing the star-shaped arrays of staples in a second radially expanded state.

Referring now to FIGS. 27A-27C, the star-shaped arrays of formed staples (90a, 90b, 90c, 90d) driven from deck member (1510) to secure tubular anatomical structures (20, 40) at anastomosis (70) may define a pair of nested undulating curvilinear staple patterns corresponding to the nested undulating curvilinear staple opening patterns defined by the star-shaped arrays of staple openings (1520a, 1520b, 1520c, 1520d). In this regard, formed staples (90a, 90b, 90c, 90d) may initially be positioned and oriented in manners corresponding to the respective staple openings (1520a, 1520b, 1520c, 1520d) so as to define the same internal angles (β1, β2) while anastomosis (70) is maintained in an unexpanded state, as shown in FIG. 27A. Formed staples (90a, 90b, 90c, 90d) may each be reoriented to accommodate expansion of at least a portion of anastomosis (70) (e.g., the inner diameter of the anastomosis (70) defined by the severed edge (60)) to one or more expanded states without stretching the puncture openings in tubular anatomical structures (20, 40) through which formed staples (90a, 90b, 90c, 90d) extend, as shown in FIGS. 27B and 27C. For example, the radially inner formed staples (90a, 90b) may each be generally pivoted about their respective radially inner and/or outer ends such that their respective radially inner ends are rotated toward each other and the radially outer formed staples (90c, 90d) may each be generally pivoted about their respective radially inner and/or outer ends such that their respective radially inner ends are rotated toward each other, thereby decreasing the first and second internal angles (β1, β2), to accommodate expansion of anastomosis (70) in a first radial direction to a first expanded state (FIG. 27B). Similarly, the radially inner formed staples (90a, 90b) may each be generally pivoted about their respective radially inner and/or outer ends such that their respective radially inner ends are rotated away from each other and the radially outer formed staples (90c, 90d) may each be generally pivoted about their respective radially inner and/or outer ends such that their respective radially inner ends are rotated away from each other, thereby increasing the first and second internal angles (β1, β2), to accommodate expansion of anastomosis (70) in a second radial direction to a second expanded state (FIG. 27C).

Figure 28:
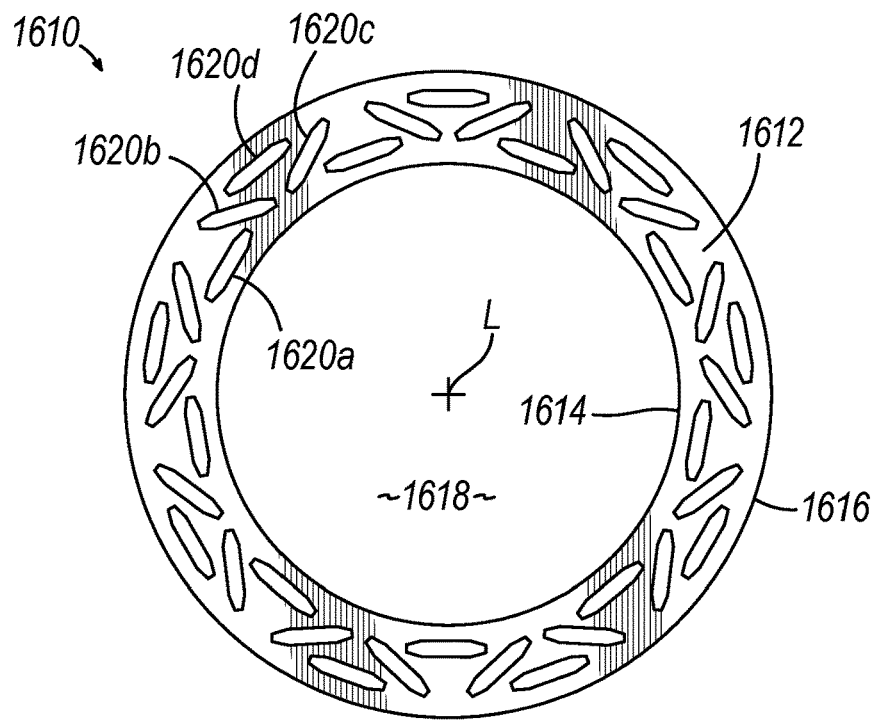
FIG. 28 depicts a top plan view of another exemplary deck member for use with the circular stapler of FIG. 1 and having three concentric annular arrays of linear staple openings arranged relative to each other in a plurality of triangle-shaped patterns.

L. Exemplary Deck Member with Staple Openings in Alternating Triangular Patterns FIG. 28 depicts an exemplary deck member (1610) for use with instrument (10) described above. Deck member (1610)

is similar to deck member (510) described above except as otherwise described below. In this regard, deck member (1610) includes a deck surface (1612) extending radially between a generally circular radially inner edge (1614) and a generally circular radially outer edge (1616). Deck member (1610) has a central opening (1618) defined by radially inner edge (1614).

Deck surface (1612) of the present version has three concentric annular arrays of linear staple openings (1620a, 1620b, 1620c, 1620d) arranged in a radially inner annular array of first staple openings (1620a), a radially intermediate annular array of circumferentially-alternating second and third staple openings (1620b, 1620c), and a radially outer annular array of fourth staple openings (1620d). As shown, each radially inner and outer staple opening (1620a, 1620d) is oriented tangentially relative to a corresponding reference circle (not shown). Each radially intermediate staple opening (1620b, 1620c) is oriented non-tangentially relative to a respective reference circle (not shown), such that each second staple opening (1620b) extends generally radially inwardly in a clockwise direction and each third staple opening (1620c) extends generally radially outwardly in a clockwise direction.

Due to the relative positions and orientations of staple openings (1620a, 1620b, 1620c, 1620d), the annular arrays of staple openings (1620a, 1620b, 1620c, 1620d) may define a plurality of alternating, generally triangular staple opening patterns. In this regard, each first staple opening (1620a), corresponding clockwise-adjacent second staple opening (1620b), and corresponding counterclockwise-adjacent third staple opening (1620c) may collectively define a respective triangular staple opening pattern, while each fourth staple opening (1620d), corresponding counterclockwise-adjacent second staple opening (1620b), and corresponding clockwise-adjacent third staple opening (1620c) may collectively define a respective triangular staple opening pattern. The alternating triangular staple opening patterns may enable the annular arrays of formed staples (90a, 90b, 90c, 90d) driven from deck member (1610) to expand radially while maintaining a secure seal, such as by creating a spring element in the staple line by providing a compressible member via rotation of the structural elements, thereby leveraging the triangular staple opening patterns to create compliance and an optimal staple pressure field. In this regard, the alternating triangular staple opening patterns may allow for three distinct pressure zones (e.g., inner, middle, and outer), and may also allow for rotation of arm elements of the triangle to "oblique" the triangle, creating compliance.

Figure 29:
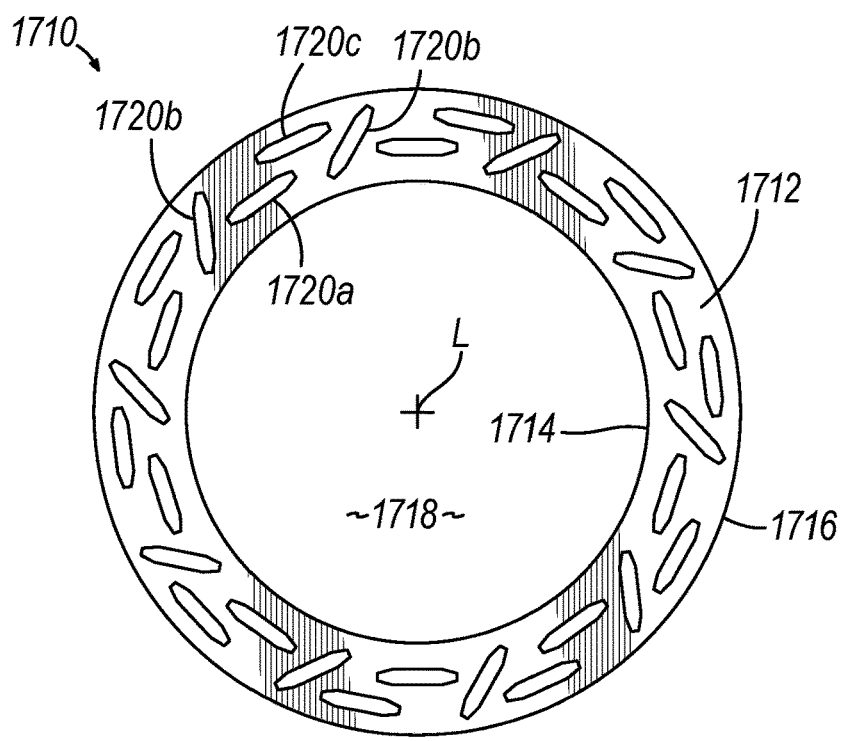
FIG. 29 depicts a top plan view of another exemplary deck member for use with the circular stapler of FIG. 1 and having three concentric annular arrays of linear staple openings arranged relative to each other in a plurality of parallelogram-shaped patterns.

M. Exemplary Deck Member with Staple Openings in Repeating Parallelogram Patterns FIG. 29 depicts an exemplary deck member (1710) for use with instrument (10) described above. Deck member (1710) is similar to deck member (510) described above except as otherwise described below. In this regard, deck member (1710) includes a deck surface (1712) extending radially between a generally circular radially inner edge (1714) and a generally circular radially outer edge (1716). Deck member (1710) has a central opening (1718) defined by radially inner edge (1714).

Deck surface (1712) of the present version has three concentric annular arrays of linear staple openings (1720a, 1720b, 1720c) arranged in a radially inner annular array of first staple openings (1720a), a radially intermediate annular array of second staple openings (1720b), and a radially outer annular array of third staple openings (1720c). As shown, each radially inner and outer staple opening (1720a, 1720c) is oriented tangentially relative to a corresponding reference circle (not shown). Each radially intermediate staple opening (1720b) is oriented non-tangentially relative to a respective reference circle (not shown), such that each second staple opening (1720b) extends generally radially outwardly in a clockwise direction.

Due to the relative positions and orientations of staple openings (1720a, 1720b, 1720c), the annular arrays of staple openings (1720a, 1720b, 1720c) may define a plurality of repeating, generally parallelogram-shaped staple opening patterns. In this regard, each first staple opening (1720a), corresponding clockwise-adjacent and counterclockwise-adjacent second staple openings (1720b), and corresponding radially-adjacent third staple opening (1720c) may collectively define a respective parallelogram-shaped staple opening pattern. The repeating parallelogram-shaped staple opening patterns may enable the annular arrays of formed staples (90a, 90b, 90c) driven from deck member (1710) to expand radially while maintaining a secure seal, such as by creating a spring element in the staple line by providing a compressible member via rotation of the structural elements, thereby leveraging the repeating parallelogram-shaped staple opening patterns to create compliance and an optimal staple pressure field. In this regard, the repeating parallelogram-shaped staple opening patterns may allow for a rotatable element of the parallelogram to create compliance, and may also allow for the pressure field to be controlled by varying the formed staple height which, in combination with uneven formed leg lengths, may allow for different pressure zones radially in the staple line.

N. Exemplary Deck Member with Staple Openings in Alternating "V" Patterns

Figure 30:
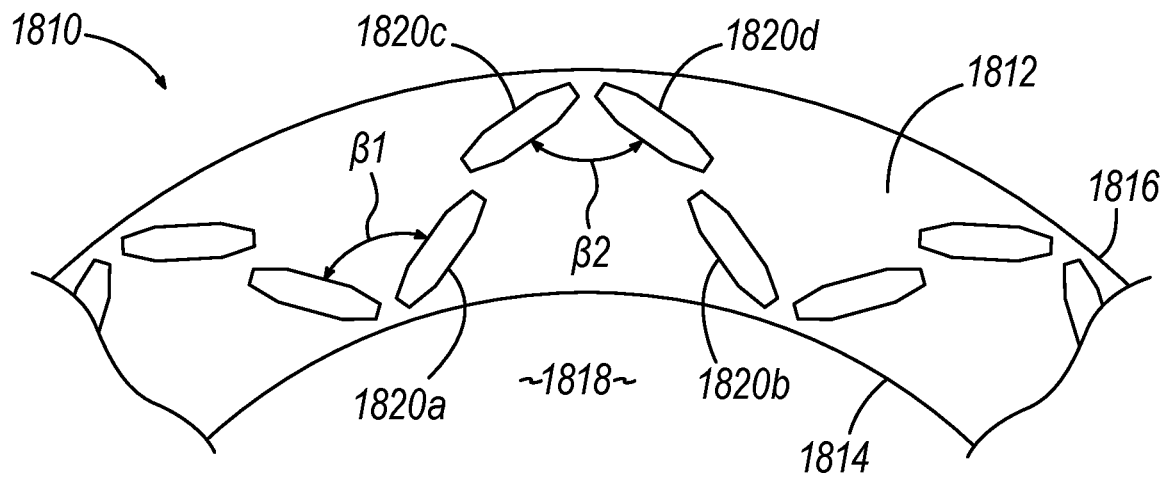
FIG. 30 depicts a partial top plan view of another exemplary deck member for use with the circular stapler of FIG. 1 and having two concentric annular arrays of linear staple openings.

FIG. 30 depicts an exemplary deck member (1810) for use with instrument (10) described above. Deck member (1810) is similar to deck member (510) described above except as otherwise described below. In this regard, deck member (1810) includes a deck surface (1812) extending radially between a generally circular radially inner edge (1814) and a generally circular radially outer edge (1816). Deck member (1810) has a central opening (1818) defined by radially inner edge (1814).

Deck surface (1812) of the present version has two concentric annular arrays of linear staple openings (1820a, 1820b, 1820c, 1820d) arranged in a radially inner annular array of circumferentially-alternating first and second staple openings (1820a, 1820b) and a radially outer annular array of circumferentially-alternating third and fourth staple openings (1820c, 1820d). As shown, each radially inner and outer staple opening (1820a, 1820b, 1820c, 1820d) is oriented non-tangentially relative to a respective reference circle (not shown), such that each first staple opening (1820a) extends generally radially outwardly in a clockwise direction, each second staple opening (1820b) extends generally radially inwardly in a clockwise direction, each third staple opening (1820c) extends generally radially outwardly in a clockwise direction, and each fourth staple opening (1820d) extends generally radially inwardly in a clockwise direction.

Due to the relative positions and orientations of staple openings (1820a, 1820b, 1820c, 1820d), the annular arrays of staple openings (1820a, 1820b, 1820c, 1820d) may define a plurality of generally V-shaped staple opening patterns. In this regard, each first staple opening (1820a) and corresponding counterclockwise-adjacent second staple opening (1820b) may collectively define a respective V-shaped staple opening pattern with a first internal angle ($\beta 1$) opening toward outer edge (1816), while each third staple opening (1820c) and corresponding clockwise-adjacent fourth staple opening (1820d) may collectively define a respective V-shaped staple opening pattern with a second internal angle (β2) opening toward inner edge (1814). In some versions, the first internal angle (β1) may be different from (e.g., greater than or less than) the second internal angle (β2). In addition, or alternatively, deck member (1810) may be used to deploy three dimensional staples (not shown) to spread the compression zone for each staple. In any event, the V-shaped staple opening patterns may enable the annular arrays of formed staples (90a, 90b, 90c, 90d) driven from deck member (1810) to expand radially while maintaining a secure seal.

O. Exemplary Deck Member with Staple Openings in Alternating "U" Patterns

Figure 31:
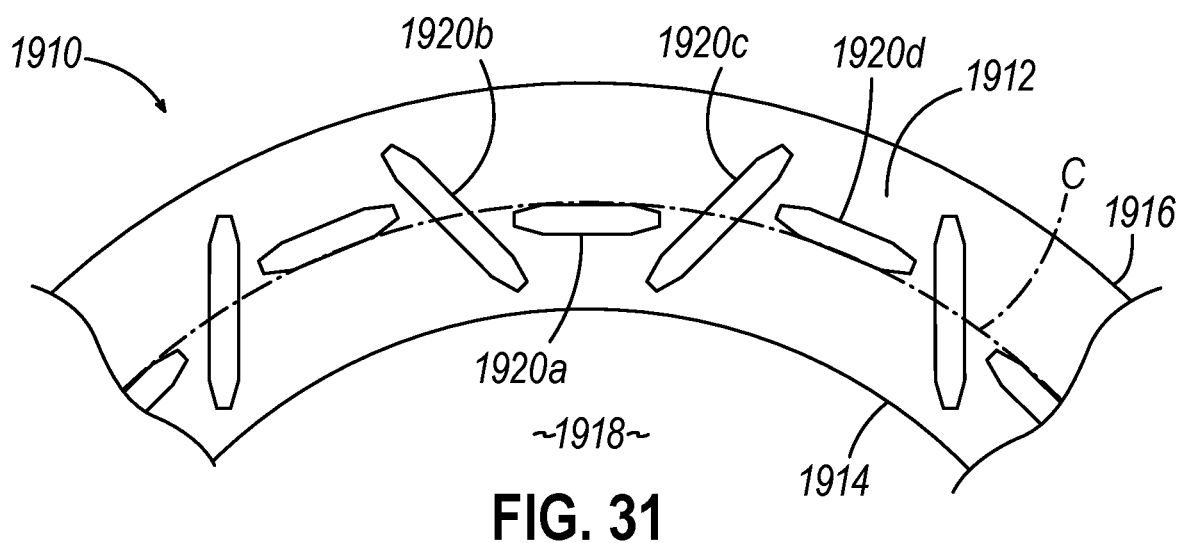
FIG. 31 depicts a partial top plan view of another exemplary deck member for use with the circular stapler of FIG. 1 and having three concentric annular arrays of linear staple openings.

FIG. 31 depicts an exemplary deck member (1910) for use with instrument (10) described above. Deck member (1910) is similar to deck member (510) described above except as otherwise described below. In this regard, deck member (1910) includes a deck surface (1912) extending radially between a generally circular radially inner edge (1914) and a generally circular radially outer edge (1916). Deck member (1910) has a central opening (1918) defined by radially inner edge (1914).

Deck surface (1912) of the present version has three concentric annular arrays of linear staple openings (1920a, 1920b, 1920c, 1920d) arranged in a radially inner annular array of first staple openings (1920a), a radially intermediate annular array of circumferentially-alternating second and third staple openings (1920b, 1920c), and a radially outer annular array of fourth staple openings (1920d). As shown, each radially inner and outer staple opening (1920a, 1920d) is oriented tangentially relative to a corresponding reference circle (not shown). Each radially intermediate staple opening (1920b, 1920c) is oriented non-tangentially relative to a respective reference circle (C), such that each second staple opening (1920b) extends generally radially inwardly in a clockwise direction and each third staple opening (1920c) extends generally radially outwardly in a clockwise direction. In the example shown, each radially inner staple opening (1920a) is positioned slightly radially inwardly relative to circle (C) such that each radially inner staple opening (1920a) is positioned closer to the radially inner ends of second and third staple openings (1920b, 1920c) than their radially outer ends, while each radially outer staple opening (1920d) is positioned slightly radially outwardly relative to circle (C) such that each radially outer staple opening (1920d) is positioned closer to the radially outer ends of second and third staple openings (1920b, 1920c) than their radially inner ends.

Due to the relative positions and orientations of staple openings (1920a, 1920b, 1920c, 1920d), the annular arrays of staple openings (1920a, 1920b, 1920c, 1920d) may define a plurality of generally U-shaped staple opening patterns. In this regard, each first staple opening (1920a), corresponding counterclockwise-adjacent second staple opening (1920b), and corresponding clockwise-adjacent third staple opening (1920c) may collectively define a respective U-shaped staple opening pattern, while each fourth staple opening (1920d), corresponding clockwise-adjacent second staple opening (1920b), and corresponding counterclockwise-adjacent third staple opening (1920c) may collectively define a respective U-shaped staple opening pattern. The U-shaped staple opening patterns may enable the annular arrays of formed staples (90a, 90b, 90c, 90d) driven from deck member (1910) to expand radially while maintaining a secure seal.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising: (a) an anvil defining a plurality of staple forming pockets; and (b) a stapling head assembly configured to drive a plurality of staples against the staple forming pockets of the anvil, wherein the stapling head assembly comprises: (i) a coupling member configured to actuate the anvil relative to the stapling head assembly, (ii) a firing assembly configured to drive the plurality of staples against the staple forming pockets of the anvil, and (iii) a deck member, comprising: (A) a deck surface extending radially between an inner circular edge and an outer circular edge, and (B) a plurality of staple openings extending through the deck surface, wherein the plurality of staple openings define at least one cross shape.

Example 2

The surgical stapling instrument of Example 1, wherein each staple opening of the plurality of staple openings includes a pair of staple opening portions, wherein the pair of staple opening portions intersect each other to collectively define the at least one cross shape.

Example 3

The surgical stapling instrument of Example 1, wherein the plurality of staple openings includes a first pair of staple openings extending along a first axis and a second pair of staple openings extending along a second axis, wherein the first and second axes intersect each other to collectively define the at least one cross shape.

Example 4

The surgical stapling instrument of any one or more of Examples 1 through 3, wherein the at least one cross shape includes four legs each having a same length.

Example 5

The surgical stapling instrument of any one or more of Examples 1 through 4, wherein the at least one cross shape includes first and second cross shapes, wherein the first and second cross shapes are circumferentially adjacent to each other.

Example 6

The surgical stapling instrument of Example 5, wherein the first and second cross shapes are spaced apart from each other by a separation distance.

Example 7

The surgical stapling instrument of Example 6, wherein the first and second cross shapes each have a width greater than the separation distance.

Example 8

The surgical stapling instrument of any one or more of Examples 5 through 7, wherein the first and second cross shapes each have a pair of radially inner ends and a pair of radially outer ends, wherein the radially inner ends are closer to each other than the radially outer ends.

Example 9

The surgical stapling instrument of any one or more of Examples 1 through 8, wherein the at least one cross shape has a crossing point, wherein the crossing point is positioned radially outwardly of a circumferential midline between the inner circular edge and the outer circular edge.

Example 10

The surgical stapling instrument of Example 9, wherein the at least one cross shape has a pair of radially inner portions and a pair of radially outer portions, wherein the radially inner ports are longer than the radially outer portions.

Example 11

The surgical stapling instrument of any one or more of Examples 1 through 10, wherein the deck member is annular, wherein the plurality of staple openings are circumferentially arranged along a reference circle.

Example 12

The surgical stapling instrument of Example 11, wherein at least a portion of the plurality of staple openings are oriented non-tangentially relative to the reference circle.

Example 13

The surgical stapling instrument of any one or more of Examples 11 through 12, wherein at least a portion of the plurality of staple openings are oriented tangentially relative to the reference circle.

Example 14

The surgical stapling instrument of any one or more of Examples 1 through 13, further comprising the plurality of staples, wherein the plurality of staples includes a pair of staples, wherein the pair of staples overlap each other to collectively define a cross shape.

Example 15

The surgical stapling instrument of any one or more of Examples 1 through 14, wherein the firing assembly includes at least one staple driver defining a cross shape.

Example 16

A surgical stapling instrument, comprising: (a) an anvil defining a plurality of staple forming pockets; and (b) a stapling head assembly configured to drive a plurality of staples against the staple forming pockets of the anvil, wherein the stapling head assembly comprises: (i) a coupling member configured to actuate the anvil relative to the stapling head assembly, (ii) a firing assembly configured to drive the plurality of staples against the staple forming pockets of the anvil, and (iii) a deck member, comprising: (A) a deck surface extending radially between an inner circular edge and an outer circular edge, and (B) a plurality of staple openings extending through the deck surface, wherein the plurality of staple openings define at least one undulating pattern having circumferentially-alternating first and second internal angles, wherein each of the first internal angles opens toward the inner circular edge, wherein each of the second internal angles opens toward the outer circular edge.

Example 17

The surgical stapling instrument of Example 16, wherein the plurality of staple openings includes: (a) a plurality of first staple openings circumferentially arranged along a first reference circle and oriented tangentially relative thereto; (b) a plurality of second staple openings circumferentially arranged along a second reference circle and oriented non-tangentially relative thereto; (c) a plurality of third staple openings circumferentially arranged along the second reference circle and oriented non-tangentially relative thereto; and (d) a plurality of fourth staple openings circumferentially arranged along a fourth reference circle and oriented tangentially relative thereto, wherein each first internal angle is defined by corresponding first, second, and third staple openings, wherein each second internal angle is defined by corresponding second, third, and fourth staple openings.

Example 18

The surgical stapling instrument of Example 17, wherein each second and third staple opening extends radially and circumferentially between corresponding first and fourth staple openings.

Example 19

The surgical stapling instrument of Example 18, further comprising a plurality of auxiliary staple openings circumferentially arranged along a fourth reference circle and oriented non-tangentially thereto, wherein the fourth reference circle is radially offset from a circumferential midline between the inner circular edge and the outer circular edge.

Example 20

A surgical stapling instrument, comprising: (a) an anvil defining a plurality of staple forming pockets; and (b) a stapling head assembly configured to drive a plurality of staples against the staple forming pockets of the anvil, wherein the stapling head assembly comprises: (i) a coupling member configured to actuate the anvil relative to the stapling head assembly, and (ii) a firing assembly configured to drive the plurality of staples against the staple forming pockets of the anvil, wherein the firing assembly includes at least one staple driver defining a cross shape.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/041,391, entitled "Methods of Forming an Anastomosis Between Organs with an Expandable Staple Pattern," filed on even date herewith; U.S. patent application Ser. No. 14/401,428, entitled "Staple Forming Features for Circular Surgical Stapler," filed on Aug. 13, 2021; U.S. patent application Ser. No. 17/401,430, entitled "Non-Circular End Effector Features for Circular Surgical Stapler," filed on Aug. 13, 2021; U.S. patent application Ser. No. 17/401,439, entitled "Circular Surgical Stapler End Effector Having Staple Line Alignment Feature," filed on Aug. 13, 2021; U.S. patent application Ser. No. 17/401,444, entitled "Circular Surgical Stapler for Forming Pattern of Non-Tangential Staples," filed on Aug. 13, 2021; and U.S. patent application Ser. No. 17/401,451, entitled "Circular Surgical Stapler Having Staples with Expandable Crowns," filed on Aug. 13, 2021. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument, comprising:
   (a) an anvil defining a plurality of staple forming pockets; and
   (b) a stapling head assembly configured to drive a plurality of staples against the staple forming pockets of the anvil, wherein the stapling head assembly comprises:
      (i) a coupling member configured to actuate the anvil relative to the stapling head assembly,
      (ii) a firing assembly configured to drive the plurality of staples against the staple forming pockets of the anvil, and
      (iii) a deck member, comprising:
         (A) a deck surface extending radially between an inner circular edge and an outer circular edge, and
         (B) a plurality of staple openings extending through the deck surface, wherein the plurality of staple openings define at least one cross shape,
         wherein the deck member is annular, wherein the plurality of staple openings are circumferentially arranged along a reference circle, wherein at least some of the plurality of staple openings are oriented non-tangentially relative to the reference circle.

2. The surgical stapling instrument of claim 1, wherein each staple opening of the plurality of staple openings includes a pair of staple opening portions, wherein the pair of staple opening portions intersect each other to collectively define the at least one cross shape.

3. The surgical stapling instrument of claim 1, wherein the plurality of staple openings includes a first pair of staple openings extending along a first axis and a second pair of staple openings extending along a second axis, wherein the first and second axes intersect each other to collectively define the at least one cross shape.

4. The surgical stapling instrument of claim 1, wherein the at least one cross shape includes four legs each having a same length.

5. The surgical stapling instrument of claim 1, wherein the at least one cross shape includes first and second cross shapes, wherein the first and second cross shapes are circumferentially adjacent to each other.

6. The surgical stapling instrument of claim 5, wherein the first and second cross shapes are spaced apart from each other by a separation distance.

7. The surgical stapling instrument of claim 6, wherein the first and second cross shapes each have a width greater than the separation distance.

8. The surgical stapling instrument of claim 5, wherein the first and second cross shapes each have a pair of radially inner ends and a pair of radially outer ends, wherein the radially inner ends are closer to each other than the radially outer ends.

9. The surgical stapling instrument of claim 1, wherein the at least one cross shape has a crossing point, wherein the crossing point is positioned radially outwardly of a circumferential midline between the inner circular edge and the outer circular edge.

10. The surgical stapling instrument of claim 9, wherein the at least one cross shape has a pair of radially inner portions and a pair of radially outer portions, wherein the radially inner portions are longer than the radially outer portions.

11. The surgical stapling instrument of claim 1, wherein at least a portion of the plurality of staple openings are oriented tangentially relative to the reference circle.

12. The surgical stapling instrument of claim 1, further comprising the plurality of staples, wherein the plurality of staples includes a pair of staples, wherein the pair of staples overlap each other to collectively define a cross shape.

13. The surgical stapling instrument of claim 1, wherein the firing assembly includes at least one staple driver defining a cross shape.

14. A surgical stapling instrument, comprising:
  (a) an anvil defining a plurality of staple forming pockets; and
  (b) a stapling head assembly configured to drive a plurality of staples against the staple forming pockets of the anvil, wherein the stapling head assembly comprises:
    (i) a coupling member configured to actuate the anvil relative to the stapling head assembly,
    (ii) a firing assembly configured to drive the plurality of staples against the staple forming pockets of the anvil, and
    (iii) a deck member, comprising:
      (A) a deck surface extending radially between an inner circular edge and an outer circular edge, and
      (B) a plurality of staple openings extending through the deck surface, wherein the plurality of staple openings define at least one undulating pattern having circumferentially-alternating first and second internal angles, wherein each of the first internal angles opens toward the inner circular edge, wherein each of the second internal angles opens toward the outer circular edge, wherein the plurality of staple openings includes:
        (1) a plurality of first staple openings circumferentially arranged along a first reference circle and oriented tangentially relative thereto,
        (2) a plurality of second staple openings circumferentially arranged along a second reference circle and oriented non-tangentially relative thereto,
        (3) a plurality of third staple openings circumferentially arranged along the second reference circle and oriented non-tangentially relative thereto, and
        (4) a plurality of fourth staple openings circumferentially arranged along a third reference circle and oriented tangentially relative thereto.

15. The surgical stapling instrument of claim 14, wherein each first internal angle is defined by corresponding first, second, and third staple openings, wherein each second internal angle is defined by corresponding second, third, and fourth staple openings.

16. The surgical stapling instrument of claim 14, wherein each second and third staple opening extends radially and circumferentially between corresponding first and fourth staple openings.

17. The surgical stapling instrument of claim 16, further comprising a plurality of auxiliary staple openings circumferentially arranged along a fourth reference circle and oriented non-tangentially thereto, wherein the fourth reference circle is radially offset from a circumferential midline between the inner circular edge and the outer circular edge.

18. A surgical stapling instrument, comprising:
  (a) an anvil defining a plurality of staple forming pockets; and
  (b) a stapling head assembly configured to drive a plurality of staples against the staple forming pockets of the anvil, wherein the stapling head assembly comprises:
    (i) a coupling member configured to actuate the anvil relative to the stapling head assembly, and
    (ii) a firing assembly configured to drive the plurality of staples against the staple forming pockets of the anvil, wherein the firing assembly includes at least one staple driver defining a cross shape.

19. The surgical stapling instrument of claim 18, wherein the at least one staple driver includes a pair of staple drivers, wherein the pair of staple drivers are integrated with each other to collectively define the at least one cross shape.

20. The surgical stapling instrument of claim 18, further comprising the plurality of staples, wherein the plurality of staples includes a pair of staples, wherein the pair of staples overlap each other to collectively define a cross shape.

* * * * *